US008865072B2

(12) United States Patent
Nagai et al.

(10) Patent No.: US 8,865,072 B2
(45) Date of Patent: Oct. 21, 2014

(54) ANALYSIS APPARATUS AND ANALYSIS METHOD

(75) Inventors: Takaaki Nagai, Kobe (JP); Yuichi Hamada, Kobe (JP); Masaharu Shibata, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 737 days.

(21) Appl. No.: 12/875,913

(22) Filed: Sep. 3, 2010

(65) Prior Publication Data
US 2010/0330609 A1 Dec. 30, 2010

Related U.S. Application Data

(63) Continuation of application No. PCT/JP2009/054247, filed on Mar. 6, 2009.

(30) Foreign Application Priority Data

| Mar. 7, 2008 | (JP) | 2008-57382 |
| Mar. 7, 2008 | (JP) | 2008-57661 |
| Mar. 7, 2008 | (JP) | 2008-57972 |
| Mar. 7, 2008 | (JP) | 2008-58007 |
| Mar. 7, 2008 | (JP) | 2008-58302 |

(51) Int. Cl.
| *G01N 33/00* | (2006.01) |
| *G01N 33/48* | (2006.01) |
| *G01N 35/02* | (2006.01) |
| *G01N 21/00* | (2006.01) |
| *G01N 15/06* | (2006.01) |
| *G01N 35/00* | (2006.01) |

(52) U.S. Cl.
CPC .... *G01N 35/026* (2013.01); *G01N 2035/00326* (2013.01); *G01N 35/0095* (2013.01); *G01N 35/0092* (2013.01)

USPC .................................. 422/67; 422/68.1; 422/73

(58) Field of Classification Search
USPC ........................................................ 422/65, 67
See application file for complete search history.

(56) References Cited

U.S. PATENT DOCUMENTS

| 5,209,903 | A | 5/1993 | Kanamori et al. |
| 5,270,012 | A | 12/1993 | Kanamori et al. |
| 5,356,595 | A | 10/1994 | Kanamori et al. |
| 5,588,555 | A | 12/1996 | Kanamori et al. |
| 5,902,549 | A | 5/1999 | Mimura et al. |
| 6,444,171 | B1 | 9/2002 | Sakazume et al. |
| 6,599,749 | B1 | 7/2003 | Kodama et al. |

(Continued)

FOREIGN PATENT DOCUMENTS

| JP | 03-094159 A | 4/1991 |
| JP | 03-279863 A | 12/1991 |

(Continued)

OTHER PUBLICATIONS

International Search Report for International Application No. PCT/JP2009/054247, dated Mar. 31, 2009, 2 pages.

*Primary Examiner* — Jill Warden
*Assistant Examiner* — Brittany Fisher
(74) *Attorney, Agent, or Firm* — Brinks Gilson & Lione

(57) ABSTRACT

This analysis apparatus includes a transporter transporting the specimens to the first measurement unit and the second measurement unit, and a control portion so controlling the transporter as to transport a first specimen container, stored in the rack, storing a first specimen to the first measurement unit and as to transport a second specimen container, stored in the rack along with the first specimen container, storing a second specimen to the second measurement unit.

17 Claims, 16 Drawing Sheets

(56) References Cited

U.S. PATENT DOCUMENTS

| | | |
|---|---|---|
| 6,733,728 B1 | 5/2004 | Mimura et al. |
| 6,772,650 B2 | 8/2004 | Ohyama et al. |
| 6,938,502 B2 | 9/2005 | Tanoshima et al. |
| 7,011,792 B2 | 3/2006 | Mimura et al. |
| 7,283,217 B2 | 10/2007 | Ikeuchi et al. |
| 7,361,305 B2 | 4/2008 | Mimura et al. |
| 7,450,223 B2 | 11/2008 | Ikeuchi et al. |
| 7,633,604 B2 | 12/2009 | Ikeuchi et al. |
| 7,700,043 B2 | 4/2010 | Mimura et al. |
| 2004/0053414 A1* | 3/2004 | Devlin, Sr. ............... 436/43 |
| 2006/0029520 A1 | 2/2006 | Tanoshima et al. |
| 2007/0110617 A1 | 5/2007 | Nagai et al. |
| 2008/0063570 A1* | 3/2008 | Fujino et al. ............. 422/99 |

FOREIGN PATENT DOCUMENTS

| | | |
|---|---|---|
| JP | 06-000770 Y2 | 1/1994 |
| JP | 06-201536 A | 7/1994 |
| JP | 08-094768 A | 4/1996 |
| JP | 09-043248 A | 2/1997 |
| JP | 09-281113 A | 10/1997 |
| JP | 2550510 Y2 | 10/1997 |
| JP | 10-090276 A | 4/1998 |
| JP | 10-282114 A | 10/1998 |
| JP | 11-064208 A | 3/1999 |
| JP | 2000-046842 A | 2/2000 |
| JP | 2000-137621 A | 5/2000 |
| JP | 2000-314737 A | 11/2000 |
| JP | 2001-074754 A | 3/2001 |
| JP | 2002-277477 A | 9/2002 |
| JP | 2003-066050 A | 3/2003 |
| JP | 2003-083960 A | 3/2003 |
| JP | 2004-226065 A | 8/2004 |
| JP | 2005-257450 A | 9/2005 |
| JP | 2007-139462 A | 6/2007 |

* cited by examiner

ANALYSIS APPARATUS AND ANALYSIS METHOD

RELATED APPLICATIONS

This application is a continuation of PCT/JP2009/054247 filed on Mar. 6, 2009, which claims priority to Japanese Application Nos. 2008-057661 filed on Mar. 7, 2008, 2008-057382 filed on Mar. 7, 2008, 2008-057972 filed on Mar. 7, 2008, 2008-058007 filed on Mar. 7, 2008, and 2008-058302 filed on Mar. 7, 2008. The entire contents of these applications are incorporated herein by reference.

BACKGROUND OF THE INVENTION

1. Field of the Invention

The present invention relates to an analysis apparatus and an analysis method.

2. Description of the Related Art

An analysis apparatus automatically transporting a plurality of specimens and analyzing the transported specimens is known in general. Such an analysis apparatus has one transporter connected to one measurement unit, and is disclosed in each of U.S. Pat. No. 7,283,217 and U.S. Patent Laying-Open No. 2007-110617, for example.

In the aforementioned analysis apparatus described in each of U.S. Pat. No. 7,283,217 and U.S. Patent Laying-Open No. 2007-110617, however, only one measurement unit is provided with respect to one transporter, and hence there has been such a problem that it is difficult to remarkably improve treatability for the specimens. While the treatability for the specimens remarkably improves if a plurality of measurement units are provided on such an analysis apparatus, on the other hand, the structure of the treatability in this case has not been known at all. If it is tried to improve the treatability for the specimens, for example, it is necessary to efficiently transport the specimens to the plurality of measurement units, and hence the size of the transporter is increased. If it is tried to miniaturize the transporter, on the other hand, the specimens cannot be efficiently transported, and the treatability for the specimens is reduced.

SUMMARY OF THE INVENTION

The scope of the present invention is defined solely by the appended claims, and is not affected to any degree by the statements within this summary.

An analysis apparatus according to a first aspect of the present invention is an analysis apparatus analyzing specimens in a plurality of specimen containers stored in a rack, including a first measurement unit measuring the specimens, a second measurement unit of the same type as the first measurement unit measuring the specimens, a transporter transporting the specimens to the first measurement unit and the second measurement unit and a control portion so controlling the transporter as to transport a first specimen container, stored in the rack, storing a first specimen to the first measurement unit and as to transport a second specimen container, stored in the rack along with the first specimen container, storing a second specimen to the second measurement unit.

An analysis method according to a second aspect of the present invention is an analysis method of analyzing specimens in a plurality of specimen containers stored in a rack, including a first transporting step of transporting a first specimen container, stored in the rack, storing a first specimen to the first measurement unit, a first incorporating step of incorporating the first specimen into the first measurement unit after the first transporting step, a second transporting step of transporting a second specimen container, stored in the rack along with the first specimen container, storing a second specimen to a second measurement unit of the same type as the first measurement unit after the first incorporating step, a second incorporating step of incorporating the second specimen into the second measurement unit after the second transporting step, a first measuring step of measuring the first specimen with the first measurement unit and a second measuring step of measuring the second specimen with the second measurement unit.

An analysis apparatus according to a third aspect of the present invention is an analysis apparatus analyzing specimens in a plurality of specimen containers stored in a rack, including a first measurement unit measuring the specimens, a second measurement unit of the same type as the first measurement unit measuring the specimens, a transporter transporting the specimens to the first measurement unit and the second measurement unit and a control portion so controlling the transporter as to distribute a plurality of specimens stored in the same rack to the first measurement unit and the second measurement unit.

DETAILED DESCRIPTION OF THE PREFERRED EMBODIMENTS

An embodiment of the present invention is now described with reference to the drawings.

First, the overall structure of a blood analysis apparatus 1 according to the embodiment of the present invention is described with reference to FIGS. 1 to 8. In this embodiment, a case of applying the present invention to the blood analysis apparatus which is an example of the analysis apparatus is described.

Figure 1:
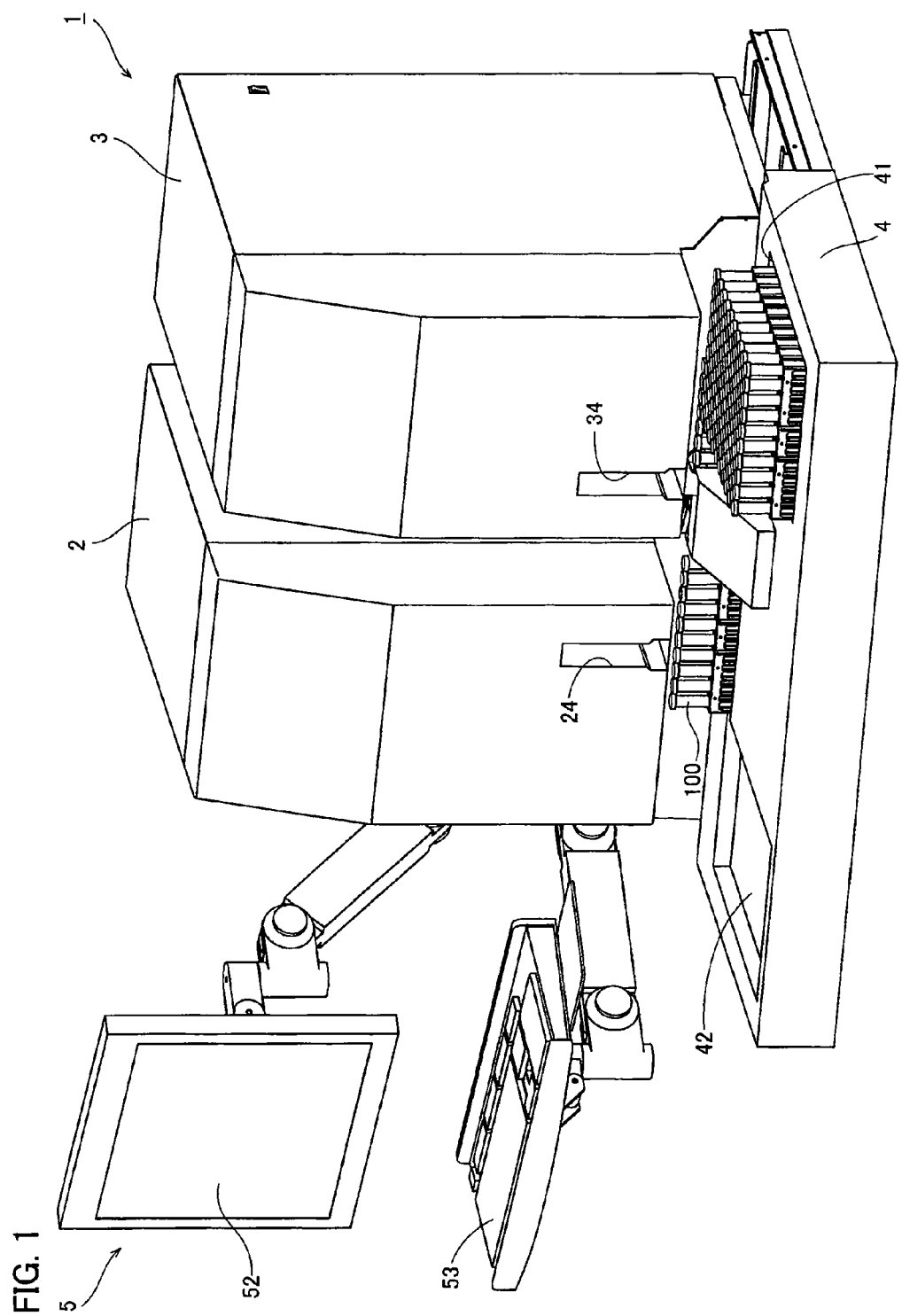
FIG. 1 is a perspective view showing the overall structure of a blood analysis apparatus according to an embodiment of the present invention.

The blood analysis apparatus 1 according to the embodiment of the present invention includes two measurement units of a first measurement unit 2 and a second measurement unit 3, a specimen transporter (sampler) 4 arranged on the side of the front surfaces of the first measurement unit 2 and the second measurement unit 3 and a controller 5 consisting of a PC (personal computer) electrically connected to the first measurement unit 2, the second measurement unit 3 and the specimen transporter 4, as shown in FIG. 1. The blood analysis apparatus 1 is connected to a host computer 6 (see FIG. 2) by the controller 5. The first measurement unit 2 and the second measurement unit 3 are measurement units of the same type, and measure specimens as to the same measurement items by employing the same measurement principle. The same type includes not only a case where the two measurement units measure the specimens as to completely identical measurement items, but also a case where a plurality of measurement items according to the first measurement unit 2 and a plurality of measurement items according to the second measurement unit 3 are partially common.

The blood analysis apparatus 1 is not a transport system connecting a plurality of analysis apparatuses with each other by a conventional transporter, but a stand-alone analysis apparatus. This blood analysis apparatus 1 may be built into a transport system.

Figure 2:
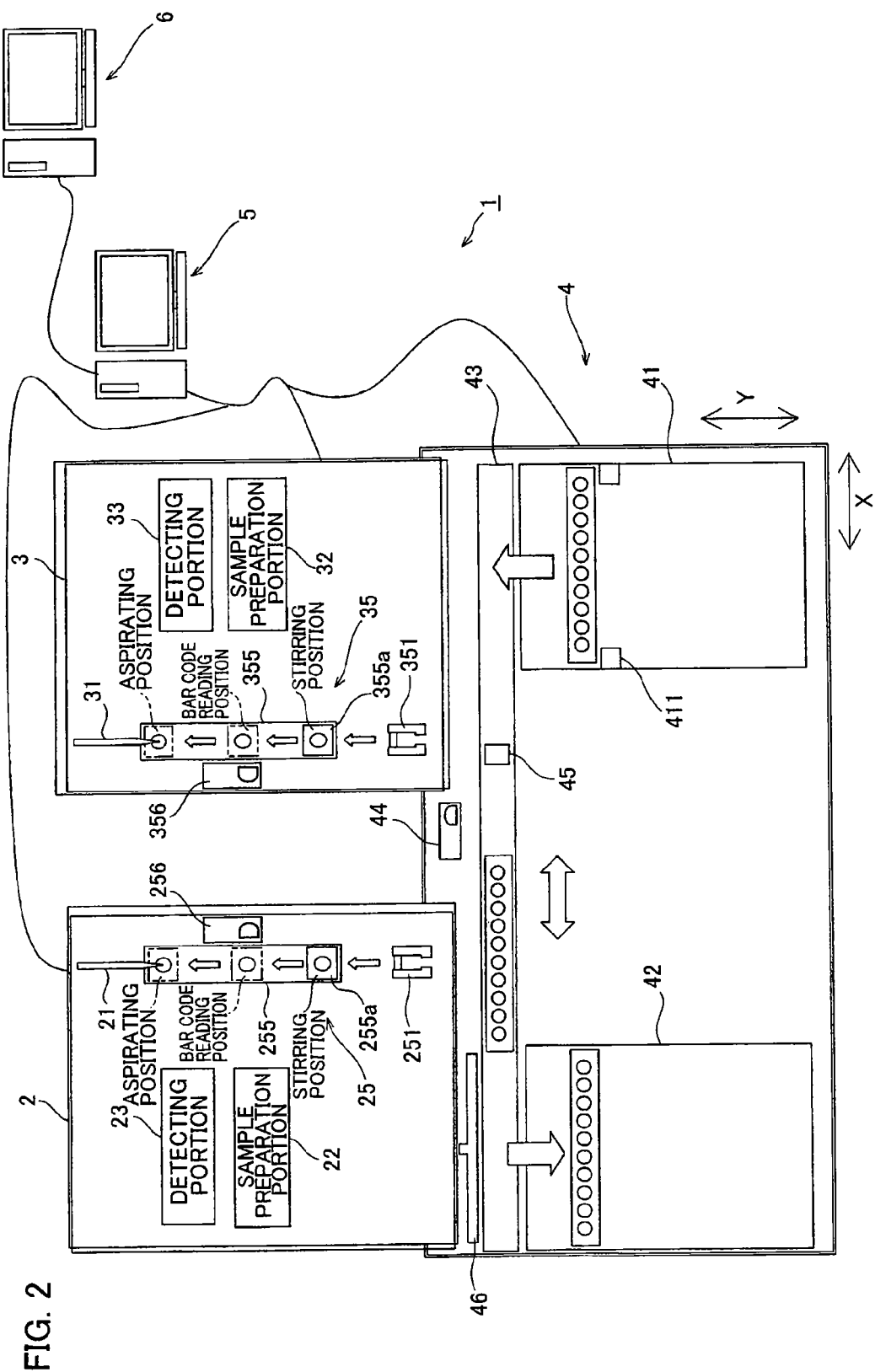
FIG. 2 is a schematic diagram showing measurement units and a specimen transporter of the blood analysis apparatus according to the embodiment of the present invention.
Figure 3:
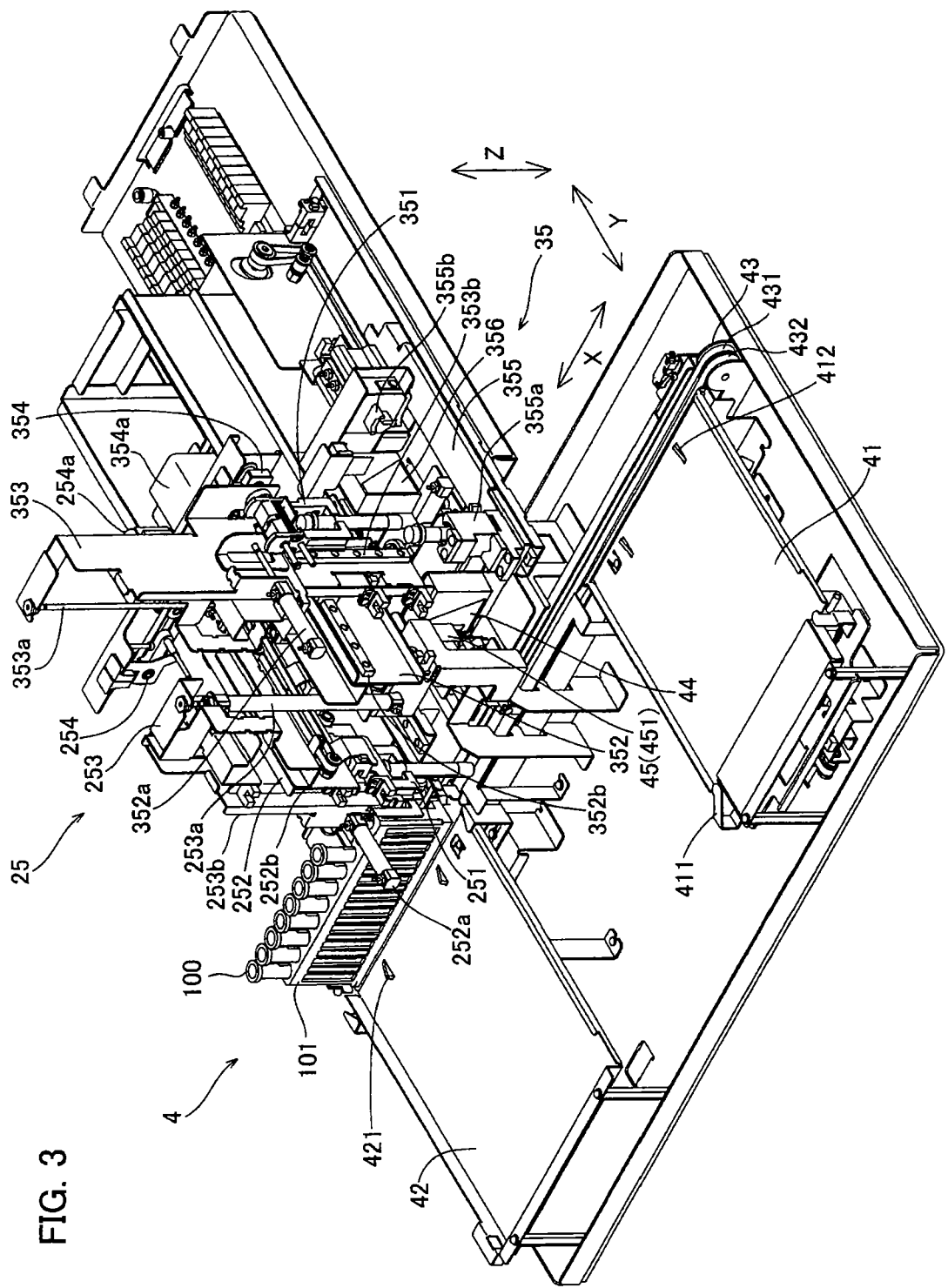
FIG. 3 is a perspective view showing the measurement units and the specimen transporter of the blood analysis apparatus according to the embodiment of the present invention.

As shown in FIGS. 1 to 3, the first measurement unit 2 and the second measurement unit 3 are arranged in the form of mirrors symmetrical with respect to the boundary between the first measurement unit 2 and the second measurement unit 3. As shown in FIG. 2, the first measurement unit 2 and the second measurement unit 3 include specimen aspirating portions 21 and 31 aspirating blood forming specimens from sample containers (test tubes) 100, sample preparation portions 22 and 32 preparing detection samples from the blood aspirated by the specimen aspirating portions 21 and 31, and a detecting portion 23 and a detecting portion 33 detecting blood cells, hemoglobin etc. from the detection samples prepared by the sample preparation portions 22 and 23 respectively. The first measurement unit 2 and the second measurement unit 3 further include incorporation ports 24 and 34 (see FIG. 1) for incorporating the sample containers 100 stored in a rack 101 (see FIG. 4) transported by the specimen transporter 4 thereinto and sample container transport portions 25 and 35 incorporating the sample containers 100 thereinto from the rack 101 and transporting the sample containers 100 to aspirating positions (see FIG. 2) by the specimen aspirating portions 21 and 31 respectively.

Needles (not shown) are provided on the forward end portions of the specimen aspirating portions 21 and 31 respectively. The specimen aspirating portions 21 and 31 are formed to be movable in the vertical direction (arrow Z direction) respectively. Further, the specimen aspirating portions 21 and 31 are formed to be moved downward thereby passing through closed lids of the sample containers 100 transported to the aspirating positions and aspirating the inner blood.

The detecting portions 23 and 33 are formed to perform RBC detection (detection of red blood cells) and PLT detection (detection of platelets) by a sheath flow DC detection method and to perform HGB detection (detection of hemoglobin in the blood) by an SLS-hemoglobin method. Further, the detecting portions 23 and 33 are formed to also perform WBC detection (detection of white blood cells) by a flow cytometry method using a semiconductor laser. Detection results obtained in the detecting portions 23 and 33 are transmitted to the controller 5 as measurement data (measurement results) of the specimens. These measurement data are data forming bases of final analytical results (numbers of red blood cells, numbers of platelets, quantities of hemoglobin, numbers of white blood cells etc.) provided to the user.

The sample container transport portions 25 and 35 respectively have hand portions 251 and 351 capable of grasping the sample containers 100, horizontal moving portions 252 and 352 horizontally linearly moving the hand portions 251 and 351 in an arrow Y direction respectively, vertical moving portions 253 and 353 linearly moving the hand portions 251 and 351 in the vertical direction (arrow Z direction) respectively and stirring portions 254 and 354 pendularly moving the hand portions 251 and 351 in the vertical direction (arrow Z direction) respectively, as shown in FIG. 3. The sample container transport portions 25 and 35 further have sample container moving portions 255 and 355 holding the sample containers 100 acquired from the rack 101 by the hand portions 251 and 351 on specimen set portions 255a and 355a and horizontally linearly moving the same to the aspirating positions of the specimen aspirating portions 21 and 31 in the arrow Y direction and bar code reading portions 256 and 356 respectively.

The hand portions 251 and 351 are formed to move to positions above the sample containers 100 stored in the rack 101 transported by the specimen transporter 4 by moving in the horizontal direction (arrow Y direction) and to thereafter grasp the sample containers 100 present thereunder by moving in the vertical direction (arrow Z direction) respectively. Then, the hand portions 251 and 351 move the grasped sample containers 100 upward, extract the same from the rack 101, and move the same to stirring positions (see FIG. 2) in the horizontal direction (arrow Y direction). The hand portions 251 and 351 are formed to be pendularly moved (by ten round trips, for example) by the stirring portions 254 and 354 on the stirring positions respectively, so that the blood in the grasped sample containers 100 is stirred. The hand portions 251 and 351 are formed to move downward after termination of the stirring thereby setting the sample containers 100 on the specimen set portions 255a and 355a of the sample container moving portions 255 and 355 and releasing the grasping.

The horizontal moving portions 252 and 352 are formed to move the hand portions 251 and 351 in the horizontal direction (arrow Y direction) along rails 252b and 352b with power by air cylinders 252a and 352a respectively.

The vertical moving portions 253 and 353 are formed to move the hand portions 251 and 351 in the vertical direction (arrow Z direction) along rails 253b and 353b with power by air cylinders 253a and 353a respectively.

The stirring portions 254 and 354 are formed to pendularly move the hand portions 251 and 351 in the vertical direction (arrow Z direction) with power by stepping motors 254a and 354a respectively.

The sample container moving portions 255 and 355 are formed to transport the specimen set portions 255a and 355a in the arrow Y direction to the aspirating positions with power by unshown stepping motors and to bring the sample containers 100 held on the specimen set portions 255a and 355a into contact with a regulating portion 355b (that on the side of the first measurement unit 2 is not shown) respectively. Thus, the same are formed to clamp (fix) the sample containers 100 on the respective aspirating positions. The sample container moving portions 255 and 355 so move the sample containers 100 to the aspirating positions in plan view that the specimen aspirating portions 21 and 31 can aspirate the samples from the sample containers 100 by simply moving in the vertical direction (arrow Z direction) without moving in the horizontal direction (arrow X and Y directions) respectively.

Figure 4:
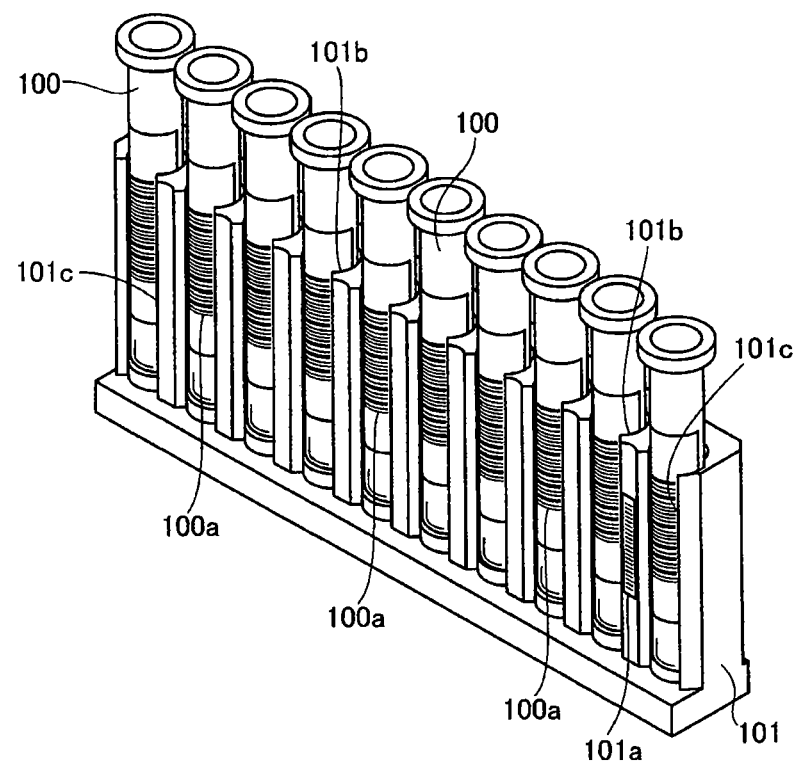
FIG. 4 is a perspective view showing a rack and sample containers of the blood analysis apparatus according to the embodiment of the present invention.

The bar code reading portions 256 and 356 are formed to read bar codes 100a, such as those shown in FIG. 4, pasted to the respective sample containers 100. Further, the bar code reading portions 256 and 356 are formed to read the bar codes 100a of the sample containers 100 while rotating the object sample containers 100 in the horizontal direction by unshown rotators in the state holding the same on the specimen set portions 255a and 355a. Thus, it is possible to direct the bar codes 100a toward the bar code reading portions 256 and 356 by rotating the sample containers 100, also in a case where the bar codes 100a of the sample containers 100 are pasted to opposite sides with respect to the bar code reading portions 256 and 356. The bar codes 100a of the respective sample containers 100 are intrinsically allotted to the respective specimens, and used for management of analytical results of the respective specimens or the like.

Figure 5:
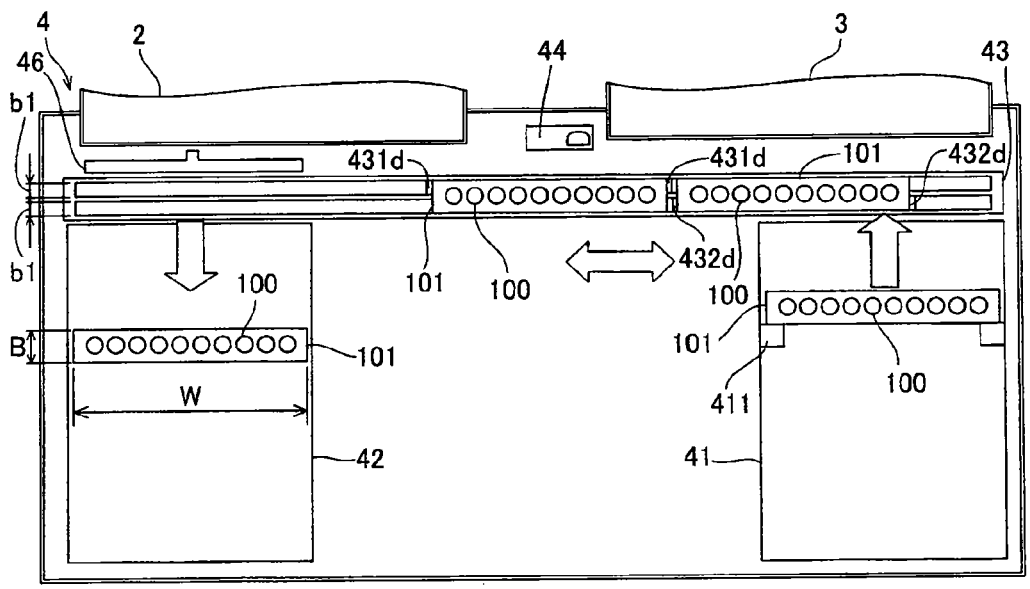
FIG. 5 is a plan view for illustrating the specimen transporter of the blood analysis apparatus according to the embodiment of the present invention.
Figure 6:
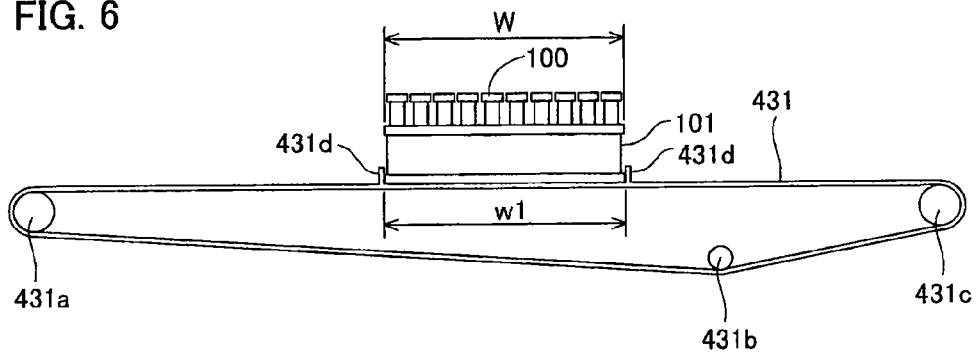
FIG. 6 is a side elevational view for illustrating the specimen transporter of the blood analysis apparatus according to the embodiment of the present invention.
Figure 7:
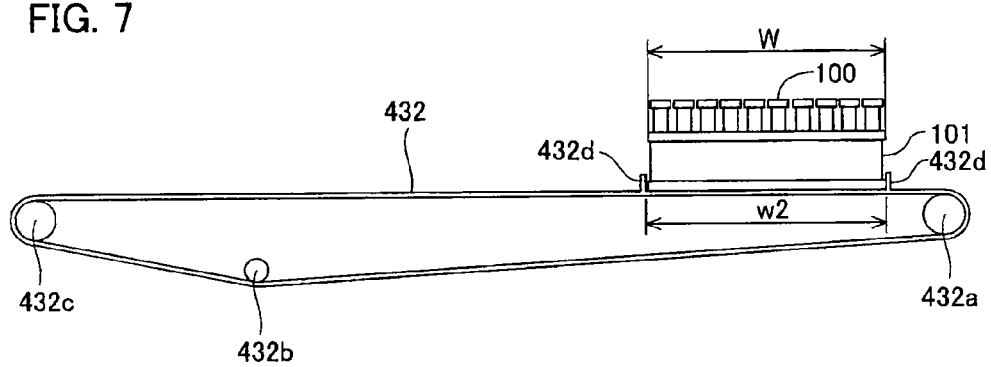
FIG. 7 is a side elevational view for illustrating the specimen transporter of the blood analysis apparatus according to the embodiment of the present invention.

According to this embodiment, the specimen transporter 4 includes a pre-analysis rack holding portion 41 capable of holding a plurality of racks 101 in which sample containers 100 storing specimens before being analyzed are stored, a post-analysis rack holding portion 42 capable of holding a plurality of racks 101 in which sample containers 100 storing specimens after being analyzed are stored, a rack transport portion 43 horizontally linearly moving the racks 101 in the arrow X direction, a bar code reading portion 44, a presence or absence sensor 45 sensing the presence or absence of the sample containers 100 and a rack delivery portion 46 moving the racks 101 into the post-analysis rack holding portion 42, as shown in FIGS. 3 and 5.

The pre-analysis rack holding portion 41 has a rack feeding portion 411, and is so formed that the rack feeding portion 411 moves in the arrow Y direction thereby pushing out the racks 101 held on the pre-analysis rack holding portion 41 one by one onto the rack transport portion 34. The rack feeding portion 411 is formed to be driven by an unshown stepping motor provided under the pre-analysis rack holding portion 41. The pre-analysis rack holding portion 41 has a regulating portion 412 (see FIG. 3) in the vicinity of the rack transport portion 43, and is formed to regulate movement of each rack 101 so that the rack 101 once pushed out onto the rack transport portion 43 is not returned into the pre-analysis rack holding portion 41.

The post-analysis rack holding portion 42 has a regulating portion 421 (see FIG. 3) in the vicinity of the rack transport portion 43, and is formed to regulate movement of each rack 101 so that the rack 101 once moved into the post-analysis rack holding portion 42 is not returned to the side of the rack transport portion 43.

The rack transport portion 43 has two belts of a first belt 431 and a second belt 432 capable of independently moving respectively. The widths b1 (see FIG. 5) of the first belt 431 and the second belt 432 in the arrow Y direction are not more than the width B of the rack 101 in the arrow Y direction respectively. Thus, both of the first belt 431 and the second belt 432 are parallelly arranged not to jut out from the width B of the rack 101 when the rack transport portion 43 transports the rack 101. Further, the first belt 431 and the second belt 432 are annularly formed, and arranged to surround rollers 431a to 431c and rollers 432a to 432c respectively. On the outer peripheral portions of the first belt 431 and the second belt 432, two protruding segments 431d and two protruding segments 432d are formed respectively to have inner widths w1 (see FIG. 6) and w2 (see FIG. 7) slightly (by about 1 mm, for example) larger than the width W of the rack 101 in the arrow X direction. The first belt 431 is formed to move the rack 101 in the arrow X direction by being moved on the outer peripheries of the rollers 431a to 431c by an unshown stepping motor in a state holding the rack 101 inside the protruding segments 431d. More specifically, the protruding segment 431d arranged on the rear side comes into contact with the rack 101 with respect to the direction of movement of the first belt 431, so that the rack 101 is moved in the direction of movement of the first belt 431 in a pushed manner. While the bottom portion of the rack 101 is in contact with the outer peripheral surface of the other second belt 432 when the rack 101 is moved, frictional force between the bottom portion of the rack 101 and the outer peripheral surface of the second belt 432 is extremely small as compared with pressing force by the protruding segment 431d in the direction of movement of the rack 101. Therefore, the first belt 431 can independently move the rack 101, regardless of the presence or absence of movement of the second belt 432. The second belt 432 is formed similarly to the first belt 431.

The bar code reading portion 44 is formed to read the bar codes 100a of the sample containers 100 shown in FIG. 4 and to read a bar code 101a pasted to the rack 101. Further, the bar code reading portion 44 is formed to read the bar codes 100a of the sample containers 100 while horizontally rotating the object sample containers 100 by an unshown rotator in the state storing the same in the rack 101. Thus, it is possible to direct the bar codes 100a toward the bar code reading portion 44 by rotating the sample containers 100, also in a case where the bar codes 100a of the sample containers 100 are pasted to opposite sides with respect to the bar code reading portion 44. The bar code 101a of the rack 101 is intrinsically allotted to each rack, and used for management of the analytical results of the specimens or the like.

The presence or absence sensor 45 is a contact type sensor, and has a curtain-shaped contact segment 451 (see FIG. 3), a light-emitting element (not shown) emitting light and a photoreceiving element (not shown). The presence or absence sensor 45 is so formed that the contact segment 451 is brought into contact with a sensed object of a target of sensing to be bent and the light emitted from the light-emitting element is reflected by the contact segment 451 and introduced into the photoreceiving element as a result. Thus, when any sample container 100 of the target of sensing stored in the rack 101 passes through a portion under the presence or absence sensor 45, the contact segment 451 is so bent by the sample container 100 that it is possible to sense that the sample container 100 is present.

The rack delivery portion 46 is arranged to be opposed to the post-analysis rack holding portion 42 through the rack transport portion 43, and formed to horizontally linearly move in the arrow Y direction. Thus, when the rack 101 is transported to the space (hereinafter referred to as a rack delivery position) between the post-analysis rack holding portion 42 and the rack delivery portion 46, it is possible to press the rack 101 and move the same into the post-analysis rack holding portion 42 by moving the rack delivery portion 46 toward the post-analysis rack holding portion 42.

Figure 8:
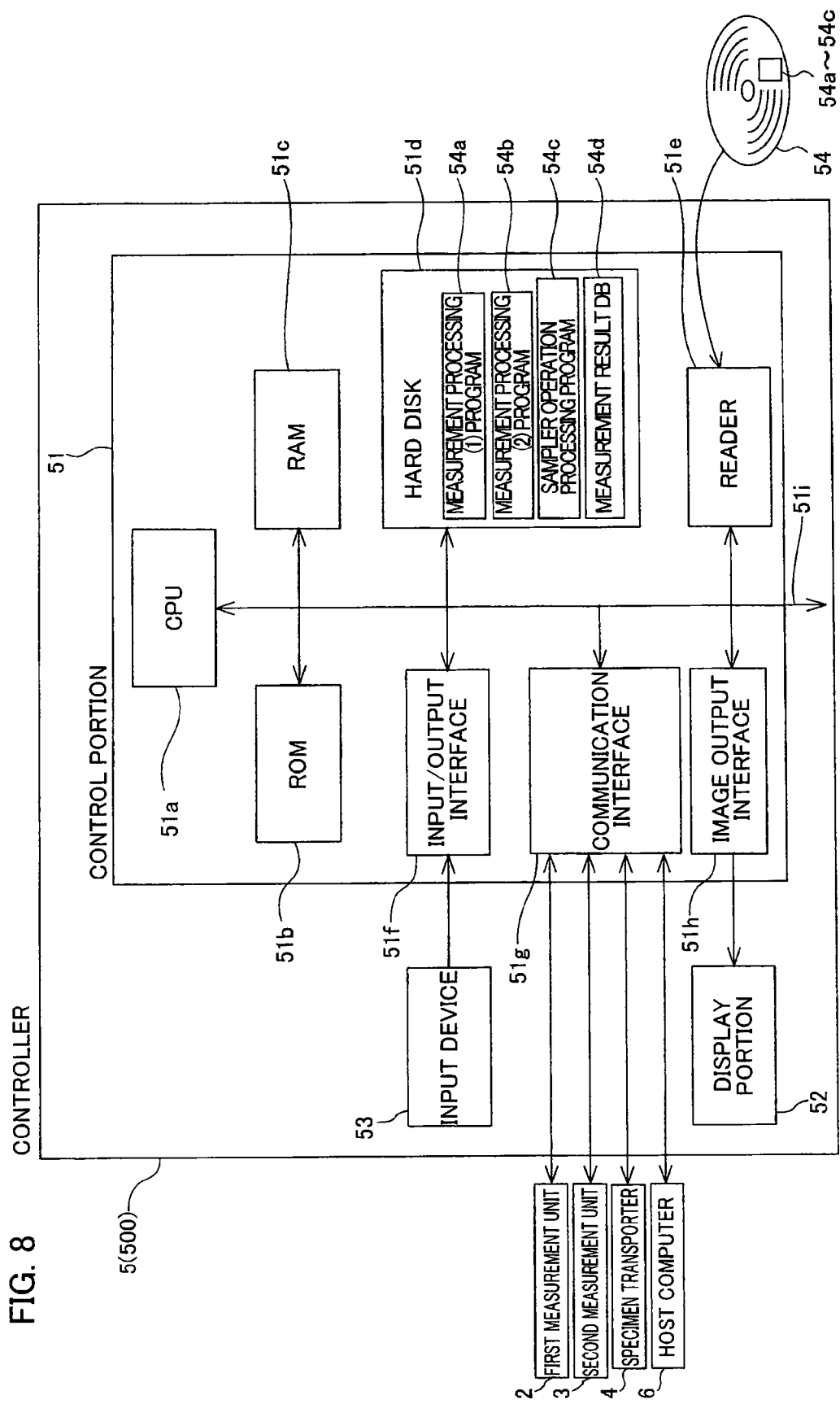
FIG. 8 is a block diagram for illustrating a controller of the blood analysis apparatus according to the embodiment of the present invention.

The controller 5 consists of a personal computer (PC) or the like, and includes a control portion 51 consisting of a CPU, a ROM, a RAM etc., a display portion 52 and an input device 53, as shown in FIGS. 1 and 8. The display portion 52 is provided for displaying analytical results or the like obtained by analyzing data of digital signals transmitted from the first measurement unit 2 and the second measurement unit 3.

The structure of the controller 5 is now described. The controller 5 is constituted of a computer 500 mainly constituted of the control portion 51, the display portion 52 and the input device 53, as shown in FIG. 8. The control portion 51 is mainly constituted of a CPU 51a, a ROM 51b, a RAM 51c, a hard disk 51d, a reader 51e, an input/output interface 51f, a communication interface 51g and an image output interface 51h. The CPU 51a, the ROM 51b, the RAM 51c, the hard disk 51d, the reader 51e, the input/output interface 51f, the communication interface 51g and the image output interface 51h are connected with each other by a bus 51i.

The CPU 51a is capable of running computer programs stored in the ROM 51b and computer programs loaded in the RAM 51c. The CPU 51a so runs application programs 54a to 54c described later that the computer 500 functions as the controller 5.

The ROM 51b is constituted of a mask ROM, a PROM, an EPROM, an EEPROM or the like, in which the computer programs run by the CPU 51a and data employed therefor are recorded.

The RAM 51c is constituted of an SRAM or a DRAM. The RAM 51c is employed for reading the computer programs recorded in the ROM 51b and the hard disk 51d. Further, the same is utilized as a working area of the CPU 51a when running these computer programs.

Various computer programs such as an operating system and application programs to be run by the CPU 51a and data employed for running the computer programs are installed in the hard disk 51d. A measurement processing program 54a for the first measurement unit 2, a measurement processing program 54b for the second measurement unit 3 and a measurement processing program 54c for the specimen transporter 4 are also installed in this hard disk 51d. These application programs 54a to 54c are so run by the CPU 51a that operations of the respective portions of the first measurement unit 2, the second measurement unit 3 and the specimen transporter 4 are controlled. A measurement result database 54d is also installed.

The reader 51e is constituted of a flexible disk drive, a CD-ROM drive or a DVD-ROM drive, and can read computer programs or data recorded in a portable recording medium 54. The application programs 54a to 54c are stored in the portable recording medium 54, and the computer 500 is capable of reading the application programs 54a to 54c from the portable recording medium 54 and installing the application programs 54a to 54c in the hard disk 51d.

The aforementioned application programs 54a to 54c are not only provided by the portable recording medium 54, but can also be provided from an external apparatus communicatively connected with the computer 500 by an electric communication line (irrespective of wired or wireless) through the aforementioned electric communication line. For example, the aforementioned application programs 54a to 54c may be stored in a hard disk of a server computer on the Internet, so that the computer 500 can download the application programs 54a to 54c and install the same in the hard disk 51d by accessing this server computer.

An operating system such as Windows (registered trademark) manufactured and sold by Microsoft Corporation, U.S.A., for example, providing a graphical user interface environment is installed in the hard disk 51d. In the following description, it is assumed that the application programs 54a to 54c operate on the aforementioned operating system.

The input/output interface 51 is constituted of a serial interface such as USB, IEEE1394 or RS-232C, a parallel interface such as SCSI, IDE or IEEE1284, or an analog interface consisting of a D/A converter, an A/D converter etc., for example. The input device 53 is connected to the input/output interface 51f, and the user can input data in the computer 500 by using the input device 53.

The communication interface 51g is an Ethernet (registered trademark) interface, for example. With the communication interface 51g, the computer 500 can transmit/receive data between the same and the first measurement unit 2, the second measurement unit 3, the specimen transporter 4 and the host computer 6 by using a prescribed communication protocol.

The image output interface 51h is connected to the display portion 52 constituted of an LCD or a CRT, to output image signals responsive to image data supplied from the CPU 51a to the display portion 52. The display portion 52 displays images (screen) according to the input image signals.

The control portion 51 is formed to analyze components of analytical objects with measurement results transmitted from the first measurement unit 2 and the second measurement unit 3 and to acquire analytical results (numbers of red blood cells, numbers of platelets, quantities of hemoglobin, numbers of white blood cells etc.), due to the aforementioned structure.

The rack 101 is provided with ten container storing portions 101b, to be capable of storing ten sample containers 100 in alignment. Openings 101c are provided on the respective container storing portions 101b, so that the bar codes 100a of the stored sample containers 100 are visually recognizable respectively.

Figure 9:
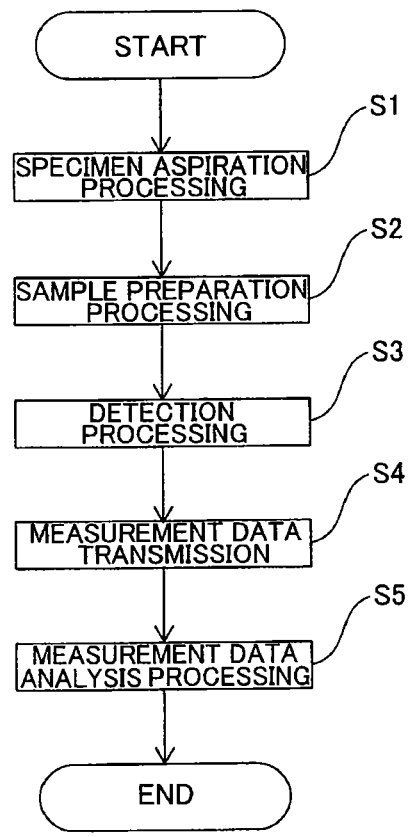
FIG. 9 is a flow chart for illustrating a measurement processing operation according to a measurement processing program of the blood analysis apparatus according to the embodiment of the present invention.
Figure 10:
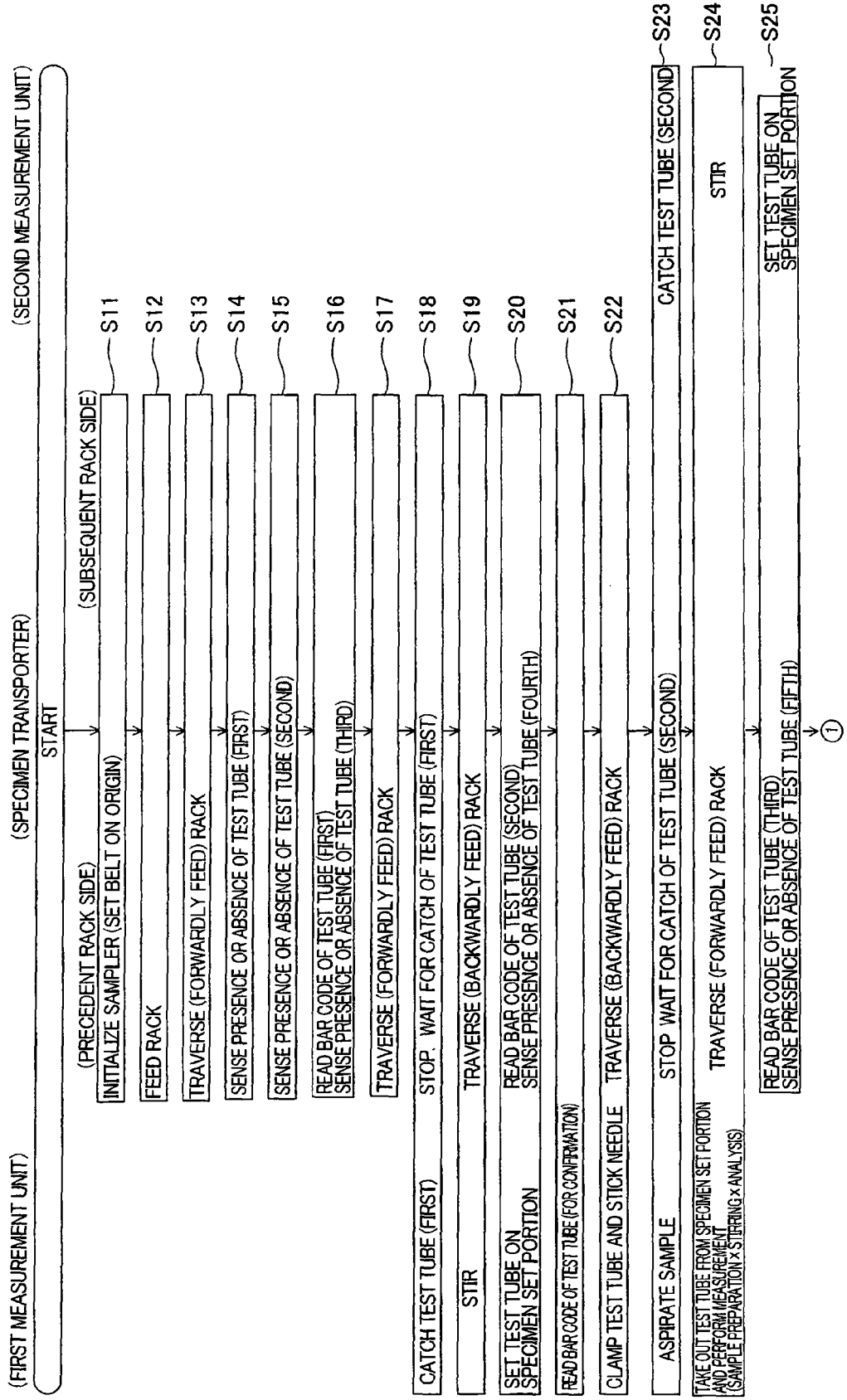
FIG. 10 is a flow chart for illustrating the contents of a measurement processing (1) program 54a, a measurement processing (2) program 54b and a sampler operation processing program 54c.
Figure 11:
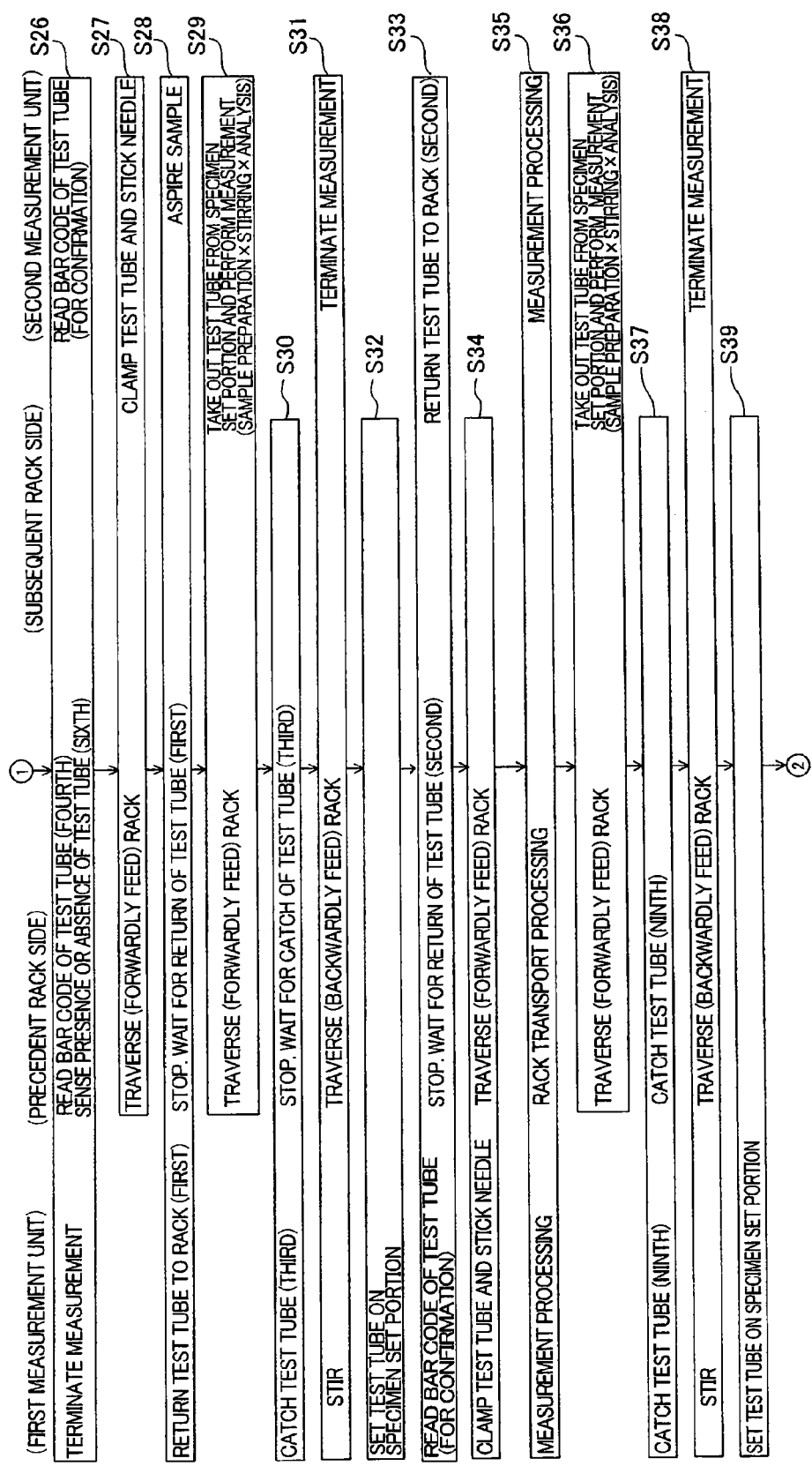
FIG. 11 is a flow chart for illustrating the contents of the measurement processing (1) program 54a, the measurement processing (2) program 54b and the sampler operation processing program 54c.
Figure 12:
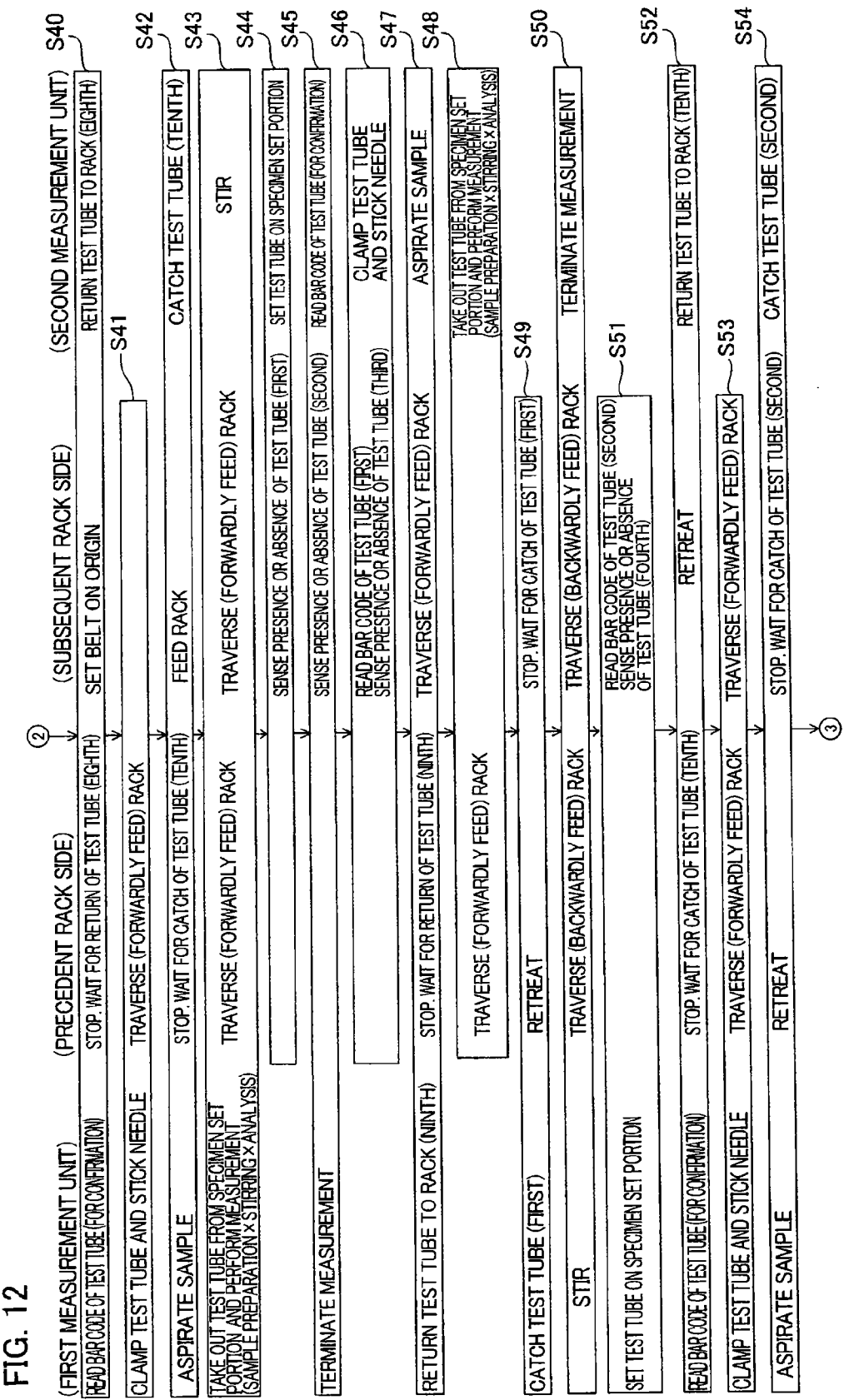
FIG. 12 is a flow chart for illustrating the contents of the measurement processing (1) program 54a, the measurement processing (2) program 54b and the sampler operation processing program 54c.
Figure 13:
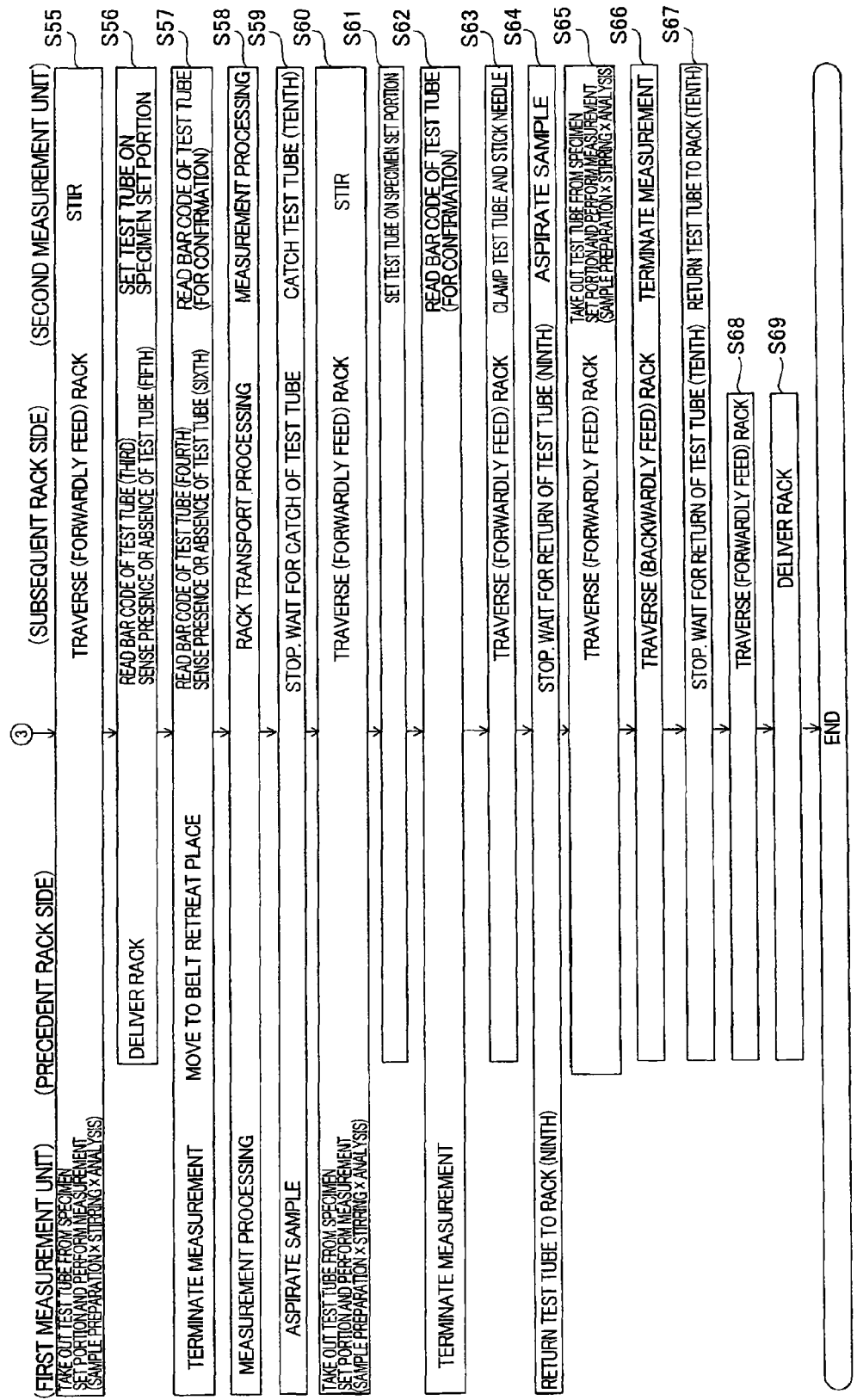
FIG. 13 is a flow chart for illustrating the contents of the measurement processing (1) program 54a, the measurement processing (2) program 54b and the sampler operation processing program 54c.

Measurement processing operations of the blood analysis apparatus 1 according to this embodiment with the measurement processing programs 54a and 54b are now described with reference to FIG. 9. Components of analytical objects are similarly measured in the first measurement unit 2 and the second measurement unit 3, and hence a case of measuring the components of the analytical object with the first measurement unit 2 is now typically described.

First, aspiration of the specimen is performed by the specimen aspirating portion 21 from any sample container 100 transported to the aspirating position (see FIG. 2) at a step S1. Then, a detection sample is prepared from the aspirated specimen by the sample preparation portion 22 at a step S2, and the components of the analytical object are detected from the detection sample by the detecting portion 23 at a step S3. Then, measurement data are transmitted from the first measurement unit 2 to the controller 5 at a step S4. Thereafter the components of the analytical object are analyzed by the control portion 51 on the basis of measurement results transmitted from the first measurement unit 2 at a step S5. Through this step S5, analysis of the specimen is completed, and the operation is terminated.

Figure 14:
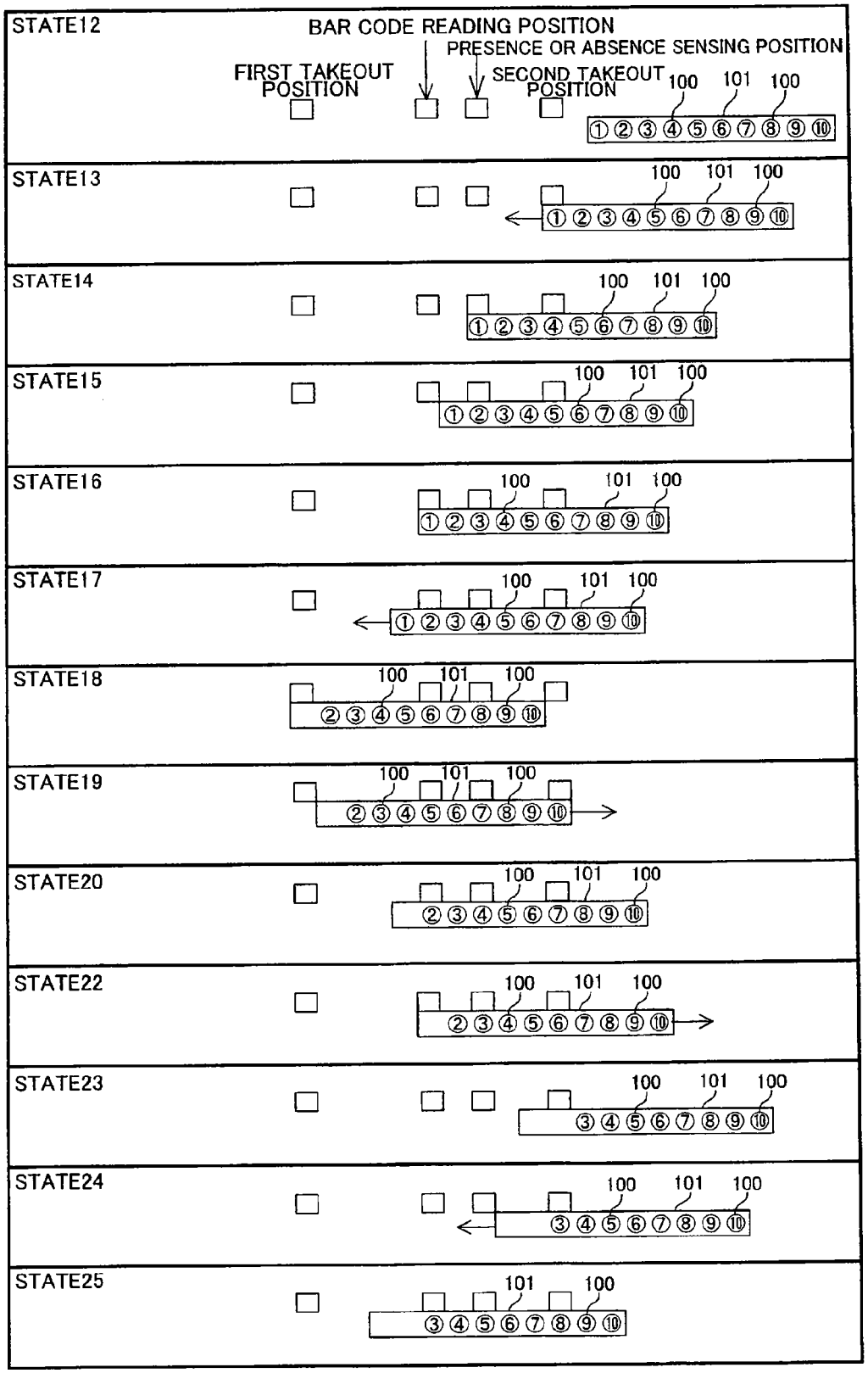
FIG. 14 is a diagram showing positional relations between the rack and the sample containers and respective portions of the blood analysis apparatus according to the embodiment of the present invention.
Figure 15:
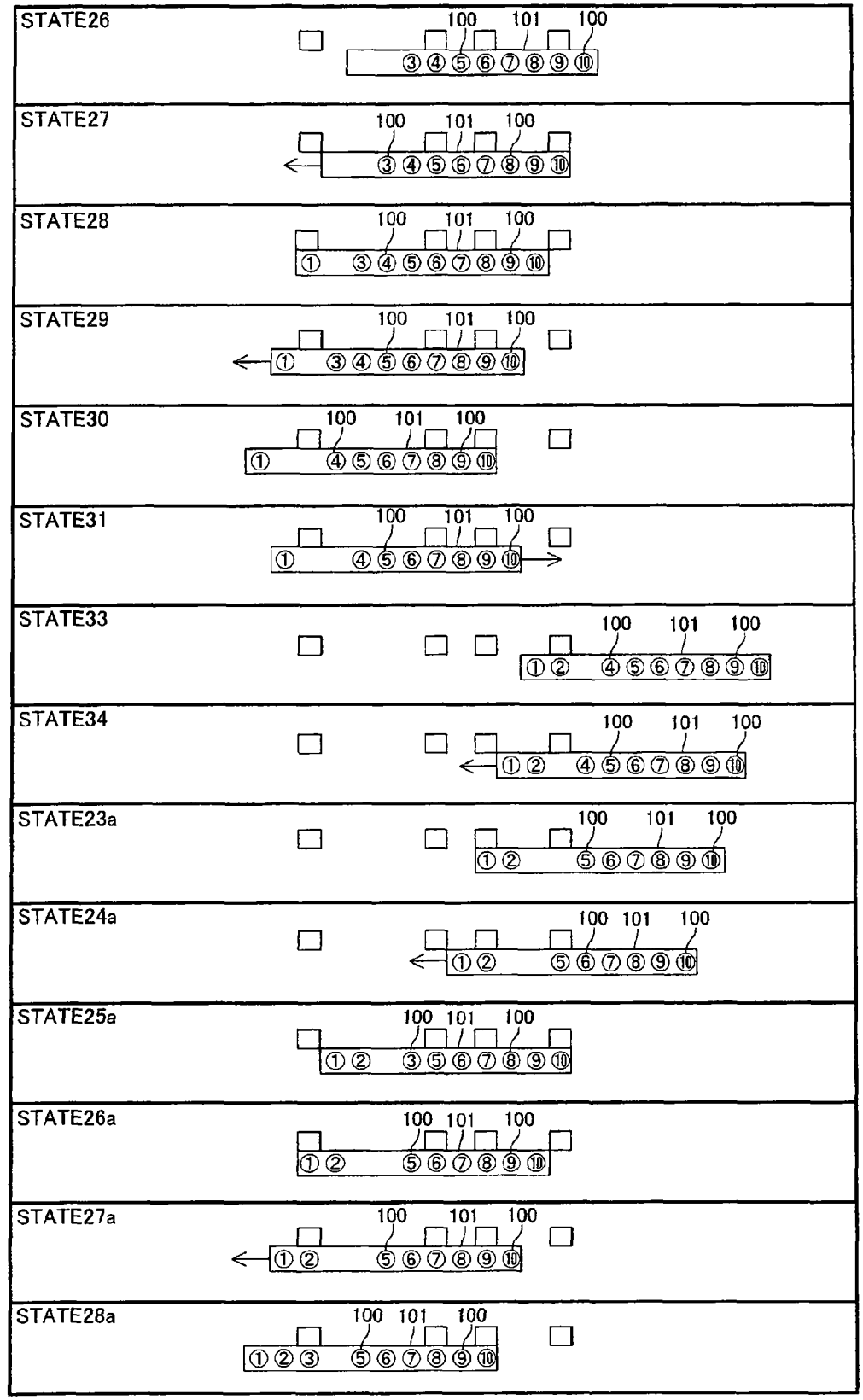
FIG. 15 is a diagram showing positional relations between the rack and the sample containers and the respective portions of the blood analysis apparatus according to the embodiment of the present invention.
Figure 16:
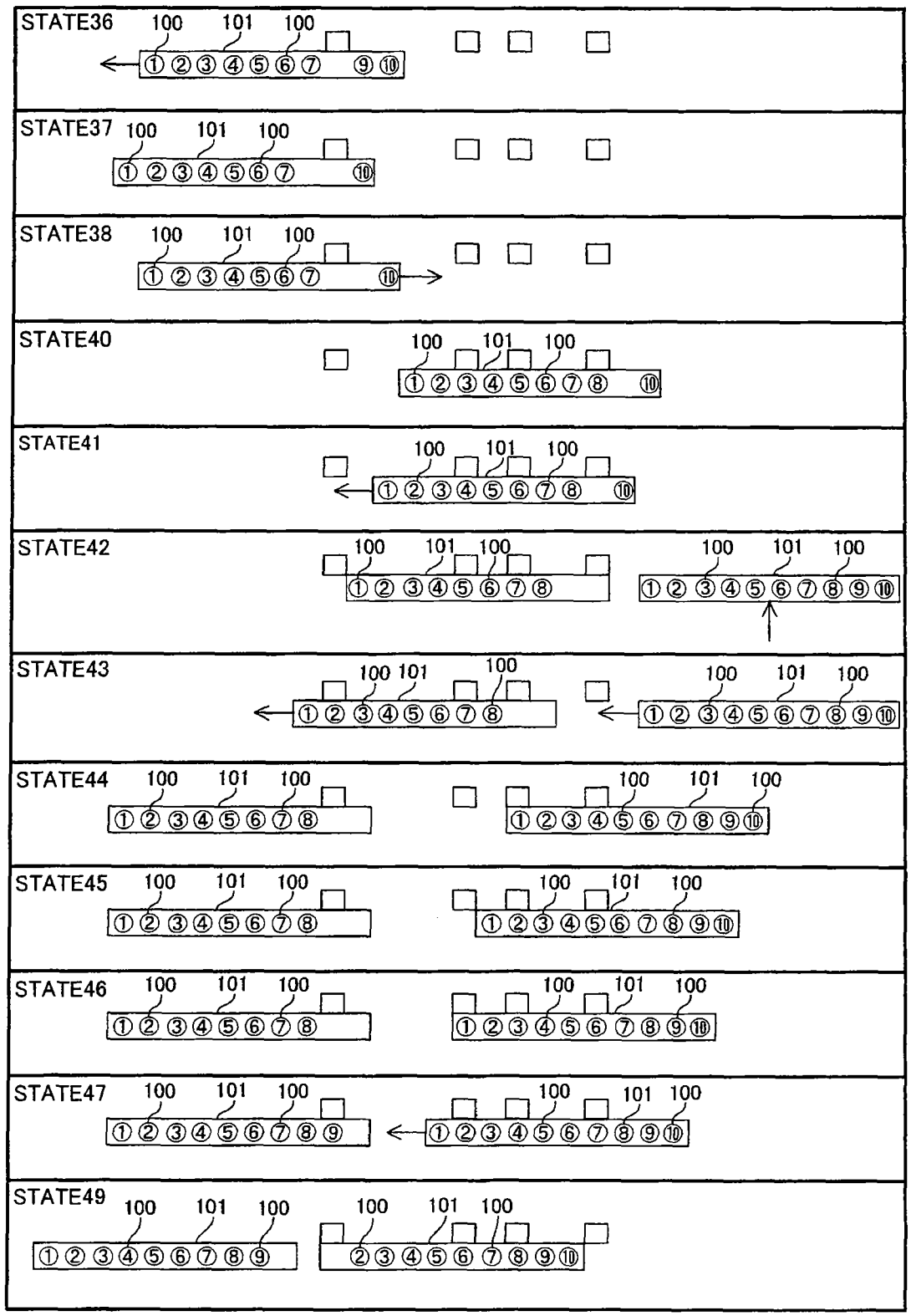
FIG. 16 is a diagram showing positional relations between racks and the sample containers and the respective portions of the blood analysis apparatus according to the embodiment of the present invention.
Figure 17:
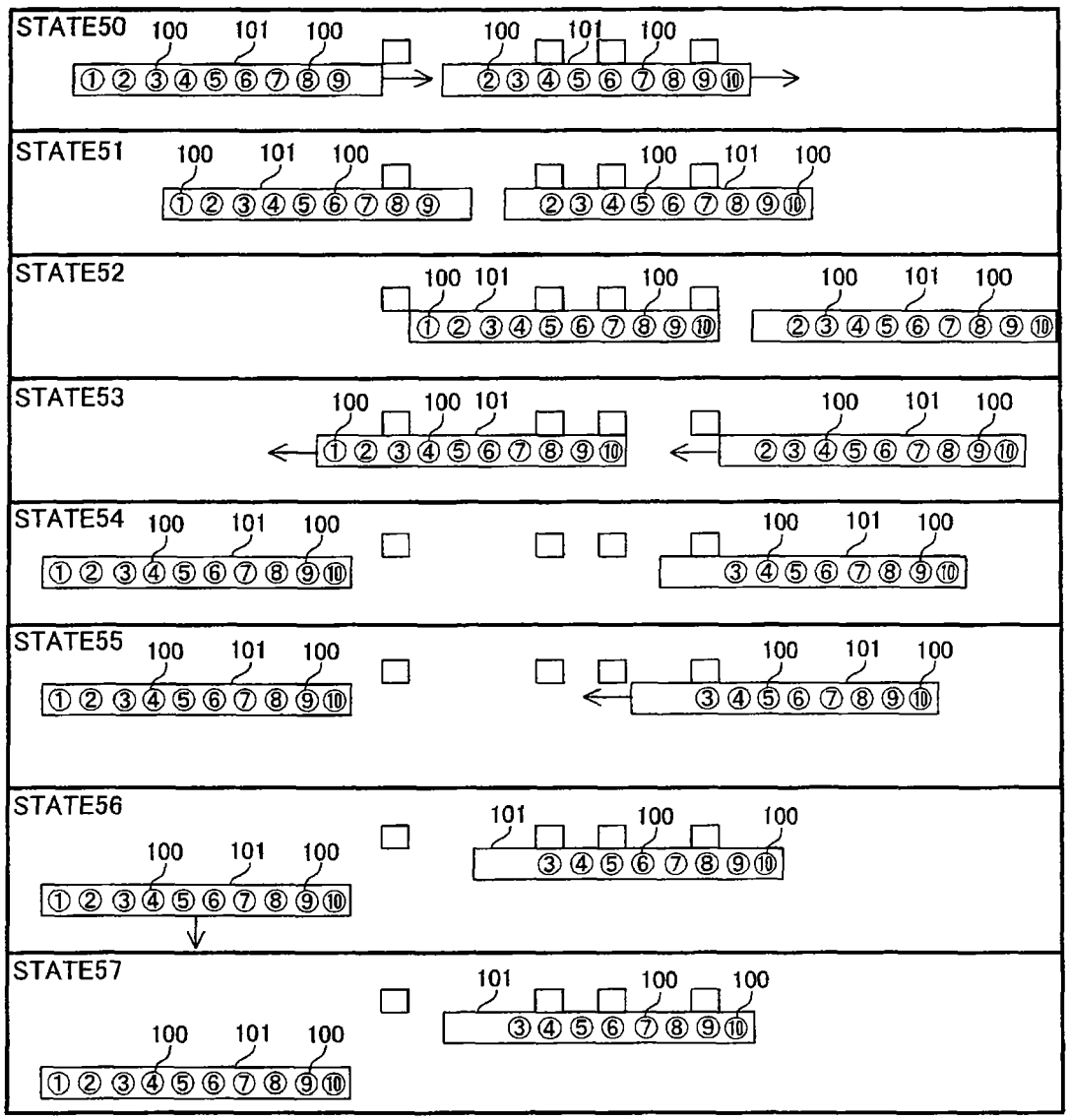
FIG. 17 is a diagram showing positional relations between the racks and the sample containers and the respective portions of the blood analysis apparatus according to the embodiment of the present invention.

A series of operations of the first measurement unit 2, the second measurement unit 3 and the specimen transporter 4 of the blood analysis apparatus 1 according to this embodiment are now described with reference to FIGS. 10 to 17. In flow charts of FIGS. 10 to 13, the contents of the measurement processing (1) program 54a are shown in the left columns and the contents of the measurement processing (2) program 54b are shown in the right columns, while the contents of the sampler operation processing program 54c are shown in the central columns. As to the sampler operation processing program 54c, processing contents related to a precedent rack 101 are shown in the left central columns, and processing contents related to a subsequent rack 101 are shown in the right central columns. The precedent rack 101 denotes a rack 101 precedently fed into the rack transport portion 43 from the pre-analysis rack holding portion 41, and the subsequent rack 101 denotes a rack 101 subsequently fed in the state where the precedent rack 101 is present on the rack transport portion 43. Numbers of respective states showing the positional relations between the racks 101 and the sample containers 100 and respective portions shown in FIGS. 14 to 17 are allotted to correspond to step numbers shown in FIGS. 10 to 13 respectively. For example, the positional relation between the rack 101 and the sample containers 100 and the respective portions in a state 13 in FIG. 14 is the positional relation between the rack 101 and the sample containers 100 and the respective portions in a step S13 shown in FIG. 10. As shown in FIGS. 10 to 13, the measurement processing (1) program 54a, the measurement processing (2) program 54b and the sampler operation processing program 54c are run substantially in parallel with each other.

In this embodiment, a case where the specimens in all sample containers 100 stored in the racks 101 are measured as to identical measurement items in the first measurement unit 2 and the second measurement unit 3.

First, when the blood analysis apparatus 1 is started by the user, initialization of the specimen transporter 4 is performed at a step S11. At this time, the protruding segments 431d of the first belt 431 are moved to prescribed positions, and set as an origin position of the first belt 431. At a step S12, the two protruding segments 431d are moved to a position (hereinafter referred to as a rack feeding position) opposed to the pre-analysis rack holding portion 41, and the precedent rack 101 is fed into the space between the two protruding segments 431d of the first belt 431. The positional relation between the rack 101 and the sample containers 100 and the respective portions at this time is the same as a state 12 in FIG. 14. In the following, description of the positional relations between the racks 101 and the sample containers 100 and the respective portions in the respective states shown in FIGS. 14 to 17 is omitted. In this embodiment, a case where first to tenth sample containers 100 are stored in each rack 101 successively from the front side toward the rear side with respect to a forward feeding direction is described, as shown in FIGS. 14 to 17.

The precedent rack 101 is moved in the direction (forward feeding direction) of the first measurement unit 2 at the step S13, and the presence or absence of the first sample container 100 stored in the precedent rack 101 is sensed by the presence or absence sensor 45 at a step S14. Then, the presence or absence of the second sample container 100 is sensed at a step S15, and the bar code 100a of the first sample container 100 is read by the bar code reading portion 44 and the presence or absence of the third is sensed at a step S16. Sensing results sensed by the presence or absence sensor 45 and bar code information read by the bar code reading portions 44, 256 and 356 are transmitted to the host computer 6 at any time. At a step S17, the precedent rack 101 is moved to a first takeout position (see FIG. 14) where the first sample container 100 is taken out from the precedent rack 101 by the hand portion 251 of the first measurement unit 2 (in other words, the first sample container 100 is transported to the first measurement unit 2). At this time, the bar code 101a of the rack 101 is read by the bar code reading portion 44. At a step S18, the first sample container 100 is taken out from the precedent rack 101 by the hand portion 251 of the first measurement unit 2. At this time, the precedent rack 101 is at a stop on a position where the first sample container 100 corresponds to the first takeout position. At a step S19, the specimen in the first sample container 100 grasped by the hand portion 251 is stirred in the first measurement unit 2, while the precedent rack 101 from which the first sample container 100 has been taken out is moved in a backward feeding direction opposite to the forward feeding direction.

At a step S20, the first sample container 100 is set on the specimen set portion 255a in the first measurement unit 2, while the bar code 100a of the second in the precedent rack 101 is read and the presence or absence of the fourth sample container 100 is sensed. The bar code 100a of the first sample container 100 is read by the bar code reading portion 256 in the first measurement unit 2 at a step S21, and the first sample container 100 held on the specimen set portion 255a is brought into contact with the regulating portion (not shown) and clamped while the needle (not shown) of the specimen aspirating portion 21 is stuck and passed into the closed lid of the sample container 100 at a step S22. At this time, the precedent rack 101 is moved to a second takeout position (see FIG. 14) where the second sample container 100 is taken out from the precedent rack 101 by the hand portion 351 of the second measurement unit 3 (in other words, the second sample container 100 is transported to the second measurement unit 3). Reading of the bar codes 100a of the sample containers 100 by the bar code reading portions 256 and 356 is performed as that for confirmation of reading by the bar code reading portion 44. Thereafter at a step S23, aspiration of the specimen in the first sample container 100 is performed by the specimen aspirating portion 21 in the first measurement unit 2, while the second sample container 100 is taken out from the precedent rack 101 by the hand portion 351 of the second measurement unit 3.

At a step S24, the first sample container 100 is taken out from the specimen set portion 255a by the hand portion 251 while sample preparation, stirring and analysis are performed as to the specimen aspirated by the specimen aspirating portion 21 in the first measurement unit 2. Further, the specimen in the second sample container 100 grasped by the hand portion 351 is stirred in the second measurement unit 3, while the precedent rack 101 is moved in the forward feeding direction. At a step S25, the second sample container 100 is set on the specimen set portion 355a in the second measurement unit 3, while the bar code 100a of the third in the precedent rack 101 is read and the presence or absence of the fifth sample container 100 is sensed. At a step S26, the measurement as to the specimen in the first sample container 100 is terminated in the first measurement unit 2, and the bar code 100a of the second sample container 100 is read by the bar code reading portion 356 in the second measurement unit 3. Further, the bar code 100a of the fourth in the precedent rack 101 is read, and the presence or absence of the sixth sample container 100 is sensed. In this description, the wording "the measurement as to the specimen is terminated" denotes transmission completion of the measurement data at the step S4 shown in FIG. 9. In other words, analytical processing (analysis) of the measurement data through the step S5 is not yet completed even if the measurement as to the specimen in the first sample container 100 is terminated at the step S26.

At a step S27, the second sample container 100 held on the specimen set portion 355a is brought into contact with the regulating portion 355b and clamped, while the needle (not shown) of the specimen aspirating portion 31 is stuck and passed into the closed lid of the sample container 100. At this time, the precedent rack 101 is moved in the forward feeding direction. At a step S28, the first sample container 100 is returned from the first measurement unit 2 into the original container storing portion 101b of the precedent rack 101, while aspiration of the specimen in the second sample container 100 is performed by the specimen aspirating portion 31 in the second measurement unit 3. At a step S29, the second sample container 100 is taken out from the specimen set portion 355a by the hand portion 351 and sample preparation, stirring and analysis are performed as to the specimen aspirated by the specimen aspirating portion 31 in the second measurement unit 3. The precedent rack 101 is moved in the forward feeding direction. At a step S30, the third sample container 100 is taken out from the precedent rack 101 by the hand portion 251 of the first measurement unit 2. At this time, the precedent rack 101 is at a stop on a position where the third sample container 100 corresponds to the first takeout position. At a step S31, the specimen in the third sample container 100 grasped by the hand portion 251 is stirred in the first measurement unit 2, while the precedent rack 101 is moved in the backward feeding direction. In the second measurement unit 3, the measurement as to the specimen in the second sample container 100 is terminated.

Then, the third sample container 100 is set on the specimen set portion 255a in the first measurement unit 2 at a step S32, and the bar code 100a of the third sample container 100 is read by the bar code reading portion 256 in the first measurement unit 2 at a step S33. Further, the second sample container 100 is returned from the second measurement unit 3 into the original container storing portion 101b of the precedent rack 101. At a step S34, the third sample container 100 is clamped, while the needle (not shown) of the specimen aspirating portion 21 is stuck and passed into the closed lid of the sample container 100. The precedent rack 101 is moved in the forward feeding direction. Also as to the following sample containers 100, measurement processing is performed in the first measurement unit 2 and the third measurement unit 3 and transport processing for the precedent rack 101 is performed in the specimen transporter 4, similarly to the above. The drawings are simplified since similar processing is repeated, and it is shown that prescribed processing is performed in each portion at a step S35. The positional relations between the precedent rack 101 and the sample containers 100 and the respective portions corresponding to the steps S23 to S28 in the repetitive processing are shown in states 23a to 28a in FIG. 15.

At a step S36, the eighth sample container 100 is taken out from the specimen set portion 355a by the hand portion 351 and sample preparation, stirring and analysis are performed as to the specimen aspirated by the specimen aspirating portion 31 in the second measurement unit 3. The precedent rack 101 is moved in the forward feeding direction. At a step S37, the ninth sample container 100 is taken out from the precedent rack 101 by the hand portion 251 of the first measurement unit 2. At this time, the precedent rack 101 is at a stop on a position where the ninth sample container 100 corresponds to the first takeout position. At a step S38, the specimen in the ninth sample container 100 is stirred in the first measurement unit 2, while the precedent rack 101 is moved in the backward feeding direction. In the second measurement unit 3, the measurement as to the specimen in the eighth sample container 100 is terminated.

The ninth sample container 100 is set on the specimen set portion 255a in the first measurement unit 2 at a step S39, and the bar code 100a of the ninth sample container 100 is read by the bar code reading portion 256 in the first measurement unit 2 at a step S40. Further, the eighth sample container 100 is returned from the second measurement unit 3 into the original container storing portion 101b of the precedent rack 101. In addition, the protruding segments 432d of the second belt 432 are moved to prescribed positions, and set as an origin position of the second belt 432. Thereafter at a step S41, the ninth sample container 100 is clamped in the first measurement unit 2, while the needle (not shown) of the specimen aspirating portion 21 is stuck and passed into the closed lid of the sample container 100. The precedent rack 101 is moved in the forward feeding direction. At a step S42, aspiration of the specimen in the ninth sample container 100 is performed by the specimen aspirating portion 21 in the first measurement unit 2, while the tenth sample container 100 is taken out from the precedent rack 101 by the hand portion 351 of the second measurement unit 3. At this time, the precedent rack 101 is at a stop so that the tenth sample container 100 comes to the second takeout position where the same is taken out by the hand portion 351. Further, the two protruding segments 432d are moved to the rack feeding position, and the subsequent rack 101 is fed into the space between the two protruding segments 432d of the second belt 432.

At a step S43, the ninth sample container 100 is taken out from the specimen set portion 255a by the hand portion 251 and sample preparation, stirring and analysis are performed as to the specimen aspirated by the specimen aspirating portion 21 in the first measurement unit 2. Further, the specimen in the tenth sample container 100 grasped by the hand portion 351 is stirred in the second measurement unit 3, while the precedent rack 101 and the subsequent rack 101 are moved in the forward feeding direction together. At a step S44, the tenth sample container 100 is set on the specimen set portion 355a in the second measurement unit 3, and the presence or absence of the first sample container 100 in the subsequent rack 101 is sensed by the presence or absence sensor 45. Thereafter at a step S45, the bar code 100a of the tenth sample container 100 is read by the bar code reading portion 356 in the second measurement unit 3, and the presence or absence of the second sample container 100 in the subsequent rack 101 is sensed by the presence or absence sensor 45.

At a step S46, the tenth sample container 100 held on the specimen set portion 355a is clamped, while the needle (not shown) of the specimen aspirating portion 31 is stuck and passed into the closed lid of the sample container 100. At this time, the bar code 100a of the first in the subsequent rack 101 is read, and the presence or absence of the third sample container 100 is sensed. At a step S47, the ninth sample container 100 is returned from the first measurement unit 2 into the original container storing portion 101b of the precedent rack 101, while aspiration of the specimen in the tenth sample container 100 is performed by the specimen aspirating portion 31 in the second measurement unit 3. Further, the subsequent rack 101 is moved in the forward feeding direction. At this time, the bar code 101*a* of the rack 101 is read by the bar code reading portion 44. At a step S48, the tenth sample container 100 is taken out from the specimen set portion 355*a* by the hand portion 351 and sample preparation, stirring and analysis are performed as to the specimen aspirated by the specimen aspirating portion 31 in the second measurement unit 3. The precedent rack 101 is moved in the forward feeding direction. At a step S49, the first sample container 100 is taken out from the subsequent rack 101 by the hand portion 251 of the first measurement unit 2. At this time, the subsequent rack 101 is at a stop on a position where the first sample container 100 corresponds to the first takeout position. Further, the precedent rack 101 retreats on a position in front of the subsequent rack 101 while the first sample container 100 is taken out from the subsequent rack 101, as shown in a state 49 in FIG. 16.

At a step S50, the specimen in the first sample container 100 of the subsequent rack 101 is stirred in the first measurement unit 2, while the precedent rack 101 and the subsequent rack 101 are moved in the backward feeding direction together. In the second measurement unit 3, the measurement as to the specimen in the tenth sample container 100 of the precedent rack 101 is terminated. At a step S51, the first sample container 100 in the subsequent rack 101 is set on the specimen set portion 255*a* in the first measurement unit 2, while the bar code 100*a* of the second in the subsequent rack 101 is read, and the presence or absence of the fourth sample container 100 is sensed. At a step S52, the bar code 100*a* of the first sample container 100 in the subsequent rack 101 is read by the bar code reading portion 256 in the first measurement unit 2. Further, the tenth sample container 100 in the precedent rack 101 is returned from the second measurement unit 3 into the original container storing portion 101*b* of the precedent rack 101. During this time, the subsequent rack 101 retreats on a position at the back of the precedent rack 101, as shown in a state 52 in FIG. 17.

At a step S53, the first sample container 100 is clamped in the first measurement unit 2, while the needle (not shown) of the specimen aspirating portion 21 is stuck and passed into the closed lid of the sample container 100. The precedent rack 101 and the subsequent rack 101 are moved in the forward feeding direction together. Thereafter at a step S54, aspiration of the specimen in the first sample container 100 is performed by the specimen aspirating portion 21 in the first measurement unit 2, while the second sample container 100 is taken out from the subsequent rack 101 by the hand portion 351 of the second measurement unit 3. At this time, the precedent rack 101 retreats on the rack delivery position, as shown in a state 54 in FIG. 17. At a step S55, the first sample container 100 is taken out from the specimen set portion 255*a* by the hand portion 251 and sample preparation, stirring and analysis are performed as to the specimen aspirated by the specimen aspirating portion 21 in the first measurement unit 2. Further, the specimen in the second sample container 100 grasped by the hand portion 351 is stirred in the second measurement unit 3, while the subsequent rack 101 is moved in the forward feeding direction.

At a step S56, the second sample container 100 is set on the specimen set portion 355*a* in the second measurement unit 3, while the bar code 100*a* of the third in the subsequent rack 101 is read, and the presence or absence of the fifth sample container 100 is sensed. The precedent rack 101 is pressed by the rack delivery portion 46, and moved into the post-analysis rack holding portion 42. At a step S57, the measurement as to the specimen in the first sample container 100 is terminated in the first measurement unit 2, and the bar code 100*a* of the second sample container 100 is read by the bar code reading portion 356 in the second measurement unit 3. Further, the bar code 100*a* of the fourth in the subsequent rack 101 is read, and the presence or absence of the sixth sample container 100 is sensed. In addition, the two protruding segments 431*d* of the first belt 431 are moved to a belt retreat place (the back side of the rack transport portion 43), not to hinder movement of the subsequent rack 101 by the second belt 432. Also as to the following sample containers 100, measurement processing is performed in the first measurement unit 2 and the second measurement unit 3 and transport processing of the subsequent rack 101 is performed in the specimen transporter 4, similarly to the above. The drawings are simplified since similar processing is repeated, and it is shown that prescribed processing is performed in each portion at a step S58.

Thereafter at a step S59, aspiration of the specimen in the ninth sample container 100 of the subsequent rack 101 is performed by the specimen aspirating portion 21 in the first measurement unit 2, while the tenth sample container 100 is taken out from the subsequent rack 101 by the hand portion 351 of the second measurement unit 3. At this time, the subsequent rack 101 is at a stop so that the tenth sample container 100 comes to the second takeout position where the same is taken out by the hand portion 351.

At a step S60, the ninth sample container 100 is taken out from the specimen set portion 255*a* by the hand portion 251 and sample preparation, stirring and analysis are performed as to the specimen aspirated by the specimen aspirating portion 21 in the first measurement unit 2. Further, the specimen in the tenth sample container 100 grasped by the hand portion 351 is stirred in the second measurement unit 3, while the subsequent rack 101 is moved in the forward feeding direction. At a step S61, the tenth sample container 100 is set on the specimen set portion 355*a* in the second measurement unit 3. Thereafter at a step S62, the measurement as to the specimen in the ninth sample container 100 is terminated in the first measurement unit 2, while the bar code 100*a* of the tenth sample container 100 is read by the bar code reading portion 356 in the second measurement unit 3. At a step S63, the tenth sample container 100 is clamped in the second measurement unit 3, while the needle (not shown) of the specimen aspirating portion 31 is stuck and passed into the closed lid of the sample container 100. At this time, the subsequent rack 101 is moved in the forward feeding direction.

At a step S64, the ninth sample container 100 is returned from the first measurement unit 2 into the original container storing portion 101*b* of the subsequent rack 101, while aspiration of the specimen in the tenth sample container 100 is performed by the specimen aspirating portion 31 in the second measurement unit 3. At a step S65, the tenth sample container 100 is taken out from the specimen set portion 355*a* by the hand portion 351 and sample preparation, stirring and analysis are performed as to the specimen aspirated by the specimen aspirating portion 31 in the second measurement unit 3. The subsequent rack 101 is moved in the forward feeding direction. At a step S66, the measurement as to the specimen in the tenth sample container 100 is terminated in the second measurement unit 3. The tenth sample container 100 is returned from the second measurement unit 3 into the original container storing portion 101*b* of the subsequent rack 101 at a step S67, while the subsequent rack 101 is moved in the forward feeding direction to the rack delivery position at a step S68. At a step S69, the subsequent rack 101 is pressed by the rack delivery portion 46 and moved into the post-analysis rack holding portion 42, and the operations are terminated. Thus, the series of operations of the first measurement unit 2, the second measurement unit 3 and the specimen transporter 4 of the blood analysis apparatus 1 according to this embodiment are performed. While the example in the case where the two racks 101 are transported has been described in this embodiment, the third and further racks 101 are fed into the rack transport portion 43 similarly to the aforementioned subsequent rack 101 fed into the rack transport portion 43 and processing is performed in each portion similarly to the above in a case where at least three racks 101 are transported.

According to this embodiment, as hereinabove described, the control portion 51 so controlling the specimen transporter 4 as to transport the first sample container 100 stored in the rack 101 to the first measurement unit 2 and as to transport the second sample container 100 stored in the rack 101 to the second measurement unit 3 is so provided that the plurality of sample containers 100 stored in the same rack 101 can be distributed to the two different measurement units 2 and 3, whereby analysis processing of the specimens can be efficiently performed. Also when measuring specimens in a final rack 101 in a case of transporting odd racks 101, for example, analysis can be performed in the two measurement units by distributing the specimens in the final rack 101 to the two measurement units 2 and 3. Therefore, analysis processing of the specimens can be efficiently performed regardless of the number of the transported racks 101. When formed as described above, the second rack 101 may not overtake the first rack 101 on the specimen transporter 4 so that it is not necessary to provide a receiving portion for the racks 101 or to provide a rack overtaking line and a rack slider on each measurement unit, whereby size increase of the blood analysis apparatus 1 can be avoided.

According to this embodiment, the first measurement unit 2 is provided with the specimen aspirating portion 21 aspirating the blood from the first sample container 100 transported by the specimen transporter 4 to the first measurement unit 2, the sample preparation portion 22 preparing the detection sample from the blood aspirated by the specimen aspirating portion 21 and the detecting portion 23 detecting blood cells, hemoglobin etc. from the detection sample prepared by the sample preparation portion 22 while the second measurement unit 3 is provided with the specimen aspirating portion 31 aspirating the blood from the second sample container 100 transported by the specimen transporter 4 to the second measurement unit 3, the sample preparation portion 32 preparing the detection sample from the blood aspirated by the specimen aspirating portion 31 and the detecting portion 33 detecting blood cells, hemoglobin etc. from the detection sample prepared by the sample preparation portion 32, whereby it is possible to aspirate the blood from the sample containers 100, to prepare the detection samples from the aspirated blood, and to detect blood cells, hemoglobin etc. from the prepared detection samples in the first measurement unit 2 and the second measurement unit 3.

According to this embodiment, the control portion 51 is formed to analyze the components of the analytical object of the detection sample detected by the detecting portion 23, to acquire analytical results of the specimen in the first sample container 100, to analyze the components of the analytical object of the detection sample detected by the detecting portion 33 and to acquire analytical results of the specimen in the second sample container 100 so that one control portion 51 analyzes both of the components detected by the detecting portion 23 and the components detected by the detecting portion 33, whereby it is not necessary to provide different control portions 51 on the respective ones of the first measurement unit 2 and the second measurement unit 3. Also according to this, miniaturization of the blood analysis apparatus 1 can be attained.

According to this embodiment, the control portion 51 is formed to control the operations of the specimen aspirating portions 21 and 31, the operations of the sample preparation portions 22 and 32, the operations of the detecting portions 23 and 33 and the operation of the specimen transporter 4 so that operation control of the respective portions can be performed with one control portion 51, whereby it is not necessary to provide separate control portions for the specimen aspirating portion 21 (31), the sample preparation portion 22 (32), the detecting portion 23 (33) and the specimen transporter 4 respectively.

According to this embodiment, the first measurement unit 2 is provided with the stirring portion 254 stirring the specimens in the sample containers 100 transported by the specimen transporter 4 and the second measurement unit 3 is provided with the stirring portion 352 stirring the specimens in the sample containers 100 transported by the specimen transporter 4, whereby analysis processing can be immediately started after the stirring. Thus, the analysis processing of the specimens can be efficiently performed.

According to this embodiment, the control portion 51 is formed to so control the specimen transporter 4 as to transport the first sample container 100 to the first measurement unit 2, as to transport the second sample container 100 to the second measurement unit 3, as to thereafter transport the third sample container 100 stored in the rack 101 to the first measurement unit 2 and as to transport the fourth sample container 100 stored in the rack 101 to the second measurement unit 3 so that the plurality of sample containers 100 stored in the same rack 101 are alternately distributed to the two measurement units 2 and 3, whereby the measurement units 2 and 3 can be continuously operated respectively.

According to this embodiment, the control portion 51 is formed to so control the specimen transporter 4 as to transport the second sample container 100 to the second measurement unit 3 before the measurement of the specimen in the first sample container 100 by the first measurement unit 2 is completed, as to transport the third sample container 100 to the first measurement unit 2 before the measurement of the specimen in the second sample container 100 by the second measurement unit 3 is completed and as to transport the fourth sample container 100 to the second measurement unit 3 before the measurement of the specimen in the third sample container 100 by the first measurement unit 2 is completed so that another sample container 100 can be incorporated into the other measurement unit while measuring the specimen in the sample container 100 transported to one measurement unit, whereby the analysis processing of the specimens can be efficiently performed.

According to this embodiment, the control portion 51 is formed to so control the specimen transporter 4 as to transport the second sample container 100 to the second measurement unit 3 before the first sample container 100 incorporated by the hand portion 251 of the first measurement unit 2 is returned from the first measurement unit 2 to the rack 101 so that the measurement of the specimen in the second sample container 100 by the second measurement unit 3 can be started earlier as compared with a case of transporting the second sample container 100 to the second measurement unit 3 after the first sample container 100 is returned from the first measurement unit 2 to the rack 101, whereby the analysis processing of the specimens can be more efficiently performed.

According to this embodiment, the measurement can be performed by the two measurement units 2 and 3 from the specimen in the sample container 100 stored in one end portion of the rack 101 by providing the rack 101 with the ten container storing portions 101b arranged in line, storing the first sample container 100 transported to the measurement unit in the first place among the plurality of sample containers 100 in the rack 101 in the container storing portion 101b arranged on one end portion among the ten container storing portions 101b arranged in line and storing the second sample container 100 transported to the measurement unit in the second place in the container storing portion 101b arranged on a second portion from the one end portion among the ten container storing portions 101b arranged in line, whereby control of the rack transportation is simplified.

According to this embodiment, the specimen transporter 4 is provided with the pre-analysis rack holding portion 41 holding the rack 101 storing the sample containers 100 in which the specimens before being analyzed by the first measurement unit 2 or the second measurement unit 3 are stored, the post-analysis rack holding portion 42 holding the rack 101 storing the sample containers 100 in which the specimens after being analyzed by the first measurement unit 2 or the second measurement unit 3 are stored and the rack transport portion 43 receiving the rack 101 from the pre-analysis rack holding portion 41 and transporting the rack 101 to the post-analysis rack holding portion 42 and the rack transport portion 43 is formed to be capable of receiving the subsequent rack 101 from the pre-analysis rack holding portion 41 before transporting the precedent rack 101 to the post-analysis rack holding portion 42 so that the rack transport portion 43 can receive the subsequent rack 101 earlier as compared with a case where the rack transport portion 43 receives the subsequent rack 101 after transporting the precedent rack 101 to the post-analysis rack holding portion 42, whereby the specimen transporter 41 can transport the sample containers 100 stored in the subsequent rack 101 to the two measurement units 2 and 3 earlier. Consequently, the analysis processing of the specimens can be efficiently performed.

According to this embodiment, the first measurement unit 2 and the second measurement unit 3 are formed to measure the specimens as to the same measurement items so that the measurement can be performed with both measurement units 2 and 3 in a case where both of the first measurement unit 2 and the second measurement unit 3 perform the measurement as to common measurable measurement items, whereby the measurement of the specimens can be rapidly performed.

According to this embodiment, the measured measurement items are equalized as to the specimens in the plurality of sample containers 100 stored in the same rack 101 so that the measurement of the specimens in the plurality of sample containers 100 stored in the same rack 101 can be performed by employing both of the first measurement unit 2 and the second measurement unit 3 whose measurement items are identical, whereby the measurement of the specimens can be rapidly performed.

According to this embodiment, the step of transporting the first sample container 100 to the first measurement unit 2 and the step of transporting the second sample container 100 to the second measurement unit 3 are so provided that the plurality of sample containers 100 stored in the same rack 101 can be distributed to the two different measurement units 2 and 3, whereby the analysis processing of the specimens can be efficiently performed. Also when measuring the specimen in the final rack 101 in the case of transporting odd racks 101, for example, the measurement can be performed in the two measurement units by distributing the specimens in the final rack 101 to the two measurement units 2 and 3. Therefore, the analysis processing of the specimens can be efficiently performed regardless of the number of the transported racks 101. When formed as described above, the second rack 101 may not overtake the first rack 101 on the specimen transporter 4 so that it is not necessary to provide a receiving portion for the racks 101 or to provide a rack overtaking line and a rack slider on each measurement unit, whereby size increase of the blood analysis apparatus 1 can be avoided.

According to this embodiment, the measurement of the specimen can be performed in the second measurement unit 3 while measuring the specimen in the first measurement unit 2 by transporting the second sample container 100 to the second measurement unit 3 before the measurement of the specimen in the first sample container 100 by the first measurement unit 2 is completed, whereby the analysis processing of the specimens can be efficiently performed.

According to this embodiment, the control portion 51 so controlling the specimen transporter 4 as to distribute the plurality of sample containers 100 stored in the same rack 101 to the first measurement unit 2 and the second measurement unit 3 is so provided that the analysis processing of the specimens can be efficiently performed. Also when measuring the specimen in the final rack 101 in the case of transporting odd racks 101, for example, the measurement can be performed in the two measurement units by distributing the specimens in the final rack 101 to the two measurement units 2 and 3. Therefore, the analysis processing of the specimens can be efficiently performed regardless of the number of the transported racks 101. When formed as described above, the second rack 101 may not overtake the first rack 101 on the specimen transporter 4 so that it is not necessary to provide a receiving portion for the racks 101 or to provide a rack overtaking line and a rack slider on each measurement unit, whereby size increase of the blood analysis apparatus 1 can be avoided.

The embodiment disclosed this time must be considered as illustrative in all points and not restrictive. The range of the present invention is shown not by the above description of the embodiment but by the scope of claims for patent, and all modifications within the meaning and range equivalent to the scope of claims for patent are further included.

For example, while the blood analysis apparatus has been shown as an example of the analysis apparatus in the aforementioned embodiment, the present invention is not restricted to this, but the present invention may be applied to another analysis apparatus so far as the same is an analysis apparatus including a plurality of measurement units.

While the example of the structure providing the stirring portions on the respective measurement units and stirring the specimens has been shown in the aforementioned embodiment, the present invention is not restricted to this, but the present invention may be applied to each of analysis apparatuses (such as a biochemical measuring apparatus and a urinalysis apparatus, for example) not stirring specimens. In this case, specimens may be aspirated from sample containers in a state stored in a rack, by moving specimen aspirating portions without providing sample container transport portions.

While the example of transporting the first sample container stored in the rack to the first measurement unit and transporting the second sample container to the second measurement unit has been shown in the aforementioned embodiment, the present invention is not restricted to this, but the first sample container may be transported to the second measurement unit, and the second sample container may be transported to the first measurement unit.

While the example of providing one control portion on the controller has been shown in the aforementioned embodiment, the present invention is not restricted to this, but different control portions may be provided on the respective ones of the first measurement unit and the second measurement unit. Further, these control portions may be built into the respective ones of the first measurement unit and the second measurement unit.

Figure 18:
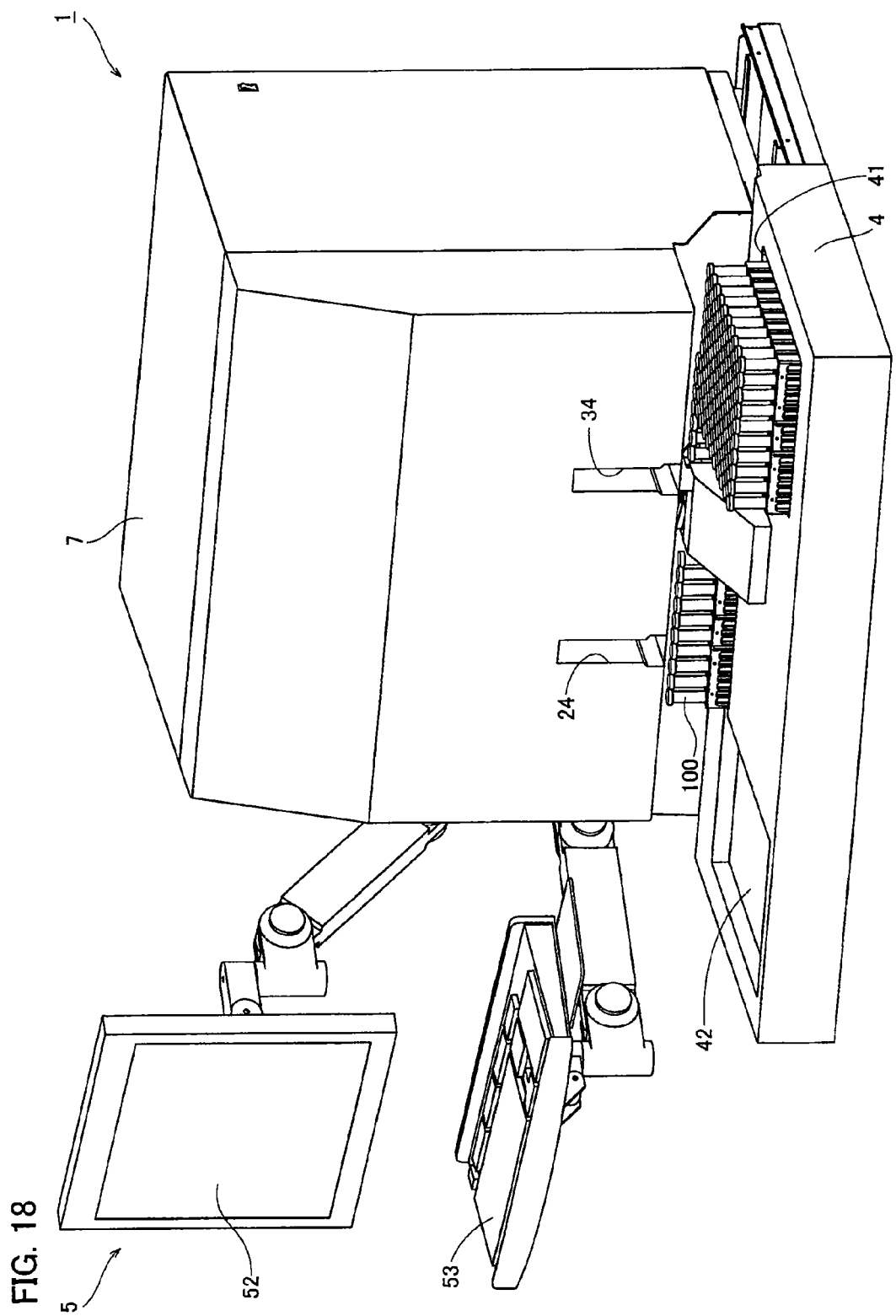
FIG. 18 is a diagram for illustrating a modification of the blood analysis apparatus according to the embodiment of the present invention.

While the example (see FIG. 1) of storing the first measurement unit and the second measurement unit in different housings independent of each other respectively has been shown in the aforementioned embodiment, the present invention is not restricted to this, but a first measurement unit and a second measurement unit may be stored in one housing 7 together, as shown in FIG. 18.

While the example of arranging the first measurement unit and the second measurement unit in the form of mirrors symmetrical with respect to the boundary between the first measurement unit and the second measurement unit has been shown in the aforementioned embodiment, the present invention is not restricted to this, but a first measurement unit and a second measurement unit having absolutely identical shapes may be adjacently arranged.

While the example in which all ten sample containers are stored in the rack has been shown in the aforementioned embodiment, the present invention is not restricted to this, but is also applicable to a case where several sample containers within the ten are not stored. In a case where there is no sample container stored in a second position of the rack, for example, a sample container stored in a third position may be analyzed as a second sample container.

What is claimed is:

1. An analysis apparatus analyzing specimens in a plurality of specimen containers stored in a rack, comprising:
  a first measurement unit configured to remove a specimen container located at a first take out position from the rack, aspirate a specimen in the specimen container, replace it to the rack and measure the aspirated specimen, wherein the first measurement unit comprises a first specimen container transport portion including a first hand portion that removes the specimen container from the first take out position of the rack and replaces it to the rack after the specimen is aspirated;
  a second measurement unit of the same type as the first measurement unit configured to remove a specimen container located at a second take out position from the rack, aspirate a specimen in the specimen container, replace it to the rack and measure the aspirated specimen, wherein the second measurement unit comprises a second specimen container transport portion including a second hand portion that removes the specimen container from the second take out position of the rack and replaces it to the rack after the specimen is aspirated;
  a transporter configured to transport the rack in a first direction from the second take out position toward the first take out position and a second direction opposite to the first direction; and
  a controller programmed to control the transporter and the first and second measurement units to carry out the steps of:
    transporting the rack storing at least first and second specimen containers in the first direction and locating the first specimen container at the first take out position;
    removing the first specimen container from the rack and aspirating a specimen;
    transporting the rack in the second direction and locating the second specimen container at the second take out position;
    removing the second specimen contained from the rack and apirating a specimen;
    transporting the rack in the first direction; and
    replacing the first specimen container in the rack.

2. The analysis apparatus according to claim 1, wherein the first measurement unit includes a first specimen aspirating portion aspirating a specimen in the specimen container removed from the rack, a first sample preparation portion preparing a detection sample from the specimen aspirated by the first specimen aspirating portion and a first detecting portion detecting a component in the detection sample prepared by the first sample preparation portion, and
  the second measurement unit includes a second specimen aspirating portion aspirating a specimen in the specimen container removed from the rack, a second sample preparation portion preparing a detection sample from the specimen aspirated by the second specimen aspirating portion and a second detecting portion detecting a component in the detection sample prepared by the second sample preparation portion.

3. The analysis apparatus according to claim 2, wherein
  the controller is further programmed to analyze the component in the detection sample detected by the first detecting portion and acquire an analytical result of the specimen, and the controller is also programmed to analyze the component in the detection sample detected by the second detecting portion and acquire an analytical result of the specimen.

4. The analysis apparatus according to claim 3, wherein
  the controller is further programmed to control operations of the first and second specimen aspirating portions, operations of the first and second sample preparation portions, operations of the first and second detecting portions and an operation of the transporter.

5. The analysis apparatus according to claim 2, wherein the first measurement unit further includes a first specimen moving portion moving the specimen container removed from the rack to an aspirating position at which the first specimen aspirating portion accesses to the specimen container, and
  the second measurement unit further includes a second specimen moving portion moving the specimen container removed from the rack to an aspirating position at which the second specimen aspirating portion accesses to the specimen container.

6. The analysis apparatus according to claim 1, wherein the first measurement unit includes a first stirring portion stirring the specimen container removed from the rack, and
  the second measurement unit includes a second stirring portion stirring the specimen container removed from the rack.

7. The analysis apparatus according to claim 1, wherein
  the first measurement unit and the second measurement unit are configured to count blood cells in a blood as the specimen.

8. The analysis apparatus according to claim 1, wherein
  the transporter includes a pre-analysis rack holding portion holding a pre-analysis rack storing a specimen container in which an unmeasured specimen is accommodated; a post-analysis rack holding portion holding a post-analysis rack storing a specimen container in which a measured specimen is accommodated; and a transport portion receiving the pre-analysis rack from the pre-analysis rack holding portion and transporting it to the post-analysis rack holding portion.

9. The analysis apparatus according to claim 1, wherein the first and second measurement units are capable of measuring specimens with respect to a common measurement item.

10. The analysis apparatus according to claim 1, wherein a measurement item measured as to the first specimen and a measurement item measured as to the second specimen are identical to each other.

11. An analysis apparatus analyzing specimens in a plurality of specimen containers stored in a rack, comprising:
a first measurement unit configured to measure a specimen in a specimen container, wherein the first measurement unit comprises a first specimen container transport portion including a first hand portion;
a second measurement unit of the same type as the first measurement unit configured to measure a specimen in a specimen container, wherein the second measurement unit comprises a second specimen container transport portion including a second hand portion;
a transporter configured to transport the rack in a first direction from the second measurement unit toward the first measurement unit and a second direction opposite to the first direction; and
a controller programmed to carry out the steps of:
transporting a rack storing a plurality of specimen containers to the first measurement unit,
extracting a first specimen container from the rack with the first hand portion and distributing the first specimen container to the first measurement unit,
transporting the rack to the second measurement unit,
extracting a second specimen container from the rack with the second hand portion and distributing the second specimen container to the second measurement unit;
transporting the rack to the first measurement unit and replacing the first specimen container into the rack using the first hand portion, and
transporting the rack to the second measurement unit and replacing the second specimen container into the rack using the second hand portion; and
wherein the transportation of the rack from the first measurement unit to the second measurement unit and from the second measurement unit to the first measurement unit occurs on a same path.

12. The analysis apparatus of claim 11, wherein the transporter includes a transport path straightly extending between a first position at which the first measurement unit accesses the specimen container stored in the rack and a second position at which the second measurement unit accesses the specimen container stored in the rack.

13. The analysis apparatus of claim 11, wherein the controller is further programmed to control the transporter to transport the rack storing at least first to third specimen containers so that the first specimen container is provided to the first measurement unit, and second specimen container is subsequently provided to the second measurement unit and the third specimen container is subsequently provided to the first measurement unit.

14. The analysis apparatus of claim 1, wherein the controller is further programmed to control the transporter to transport the rack in the second direction so that the second specimen container is replaced in the rack.

15. The analysis apparatus of claim 14, wherein the controller is further programmed to control the transporter to transport the rack in the first or second direction so that a third specimen container additionally stored in the rack is located at the first take out position after the first measurement unit replaced the first specimen container in the rack.

16. The analysis apparatus of claim 1, wherein the transporter includes a transport path straightly extending between the first take out position and the second take out position and is configured to transport the rack on the transport path in both of the first and second directions.

17. The analysis apparatus of claim 6, wherein the first stirring portion is configured to catch a specimen container located at the first take out position and swing it several times, and the first measurement unit is configured to aspirate a specimen in the specimen container after completion of the swings, and the second stirring portion is configured to catch a specimen container located at the second take out position and swing it several times, and the second measurement unit is configured to aspirate a specimen in the specimen container after completion of the swings.

* * * * *